US 7,842,278 B2

(12) United States Patent
Lee et al.

(10) Patent No.: US 7,842,278 B2
(45) Date of Patent: *Nov. 30, 2010

(54) HYPOXIA-SELECTIVE, WEAKLY BASIC 2-NITROIMIDAZOLE DELIVERY AGENTS AND METHODS OF USE THEREOF

(75) Inventors: David Y-W Lee, Cambridge, MA (US); Xiao-Shen Ji, Acton, MA (US); James A. Raleigh, Chapel Hill, NC (US)

(73) Assignee: Natural Pharmacia International, Inc., Burlington, MA (US)

( * ) Notice: Subject to any disclaimer, the term of this patent is extended or adjusted under 35 U.S.C. 154(b) by 360 days.

This patent is subject to a terminal disclaimer.

(21) Appl. No.: 11/588,634

(22) Filed: Oct. 27, 2006

(65) Prior Publication Data

US 2008/0102026 A1 May 1, 2008

(51) Int. Cl.
*A61K 51/00* (2006.01)
*A61M 36/14* (2006.01)

(52) U.S. Cl. .................... 424/1.65; 424/1.11; 424/1.81; 424/1.85; 424/1.89; 548/300.1; 548/327.1; 548/327.5

(58) Field of Classification Search ................. 424/1.11, 424/1.65, 1.69, 1.73, 1.81, 1.85, 1.89, 9.1; 548/100, 300.1, 325.5, 327.1, 327.5
See application file for complete search history.

(56) References Cited

U.S. PATENT DOCUMENTS

| 4,282,232 A | | 8/1981 | Agrawal |
| 5,387,692 A | * | 2/1995 | Riley et al. ............... 548/313.7 |
| 5,674,693 A | * | 10/1997 | Raleigh et al. ............. 435/7.23 |
| 2008/0085237 A1 | | 4/2008 | Raleigh et al. |

FOREIGN PATENT DOCUMENTS

| EP | 0 302 416 | 2/1989 |
| WO | WO 2008/063749 | 5/2008 |

OTHER PUBLICATIONS

Naylor et al, Journal of Medicinal Chemistry, 1990, vol. 33, No. 9, pp. 2508-2513.*
Barth et al., "Boron Neutron Capture Therapy for Cancer. Realities and Prospects," *Cancer* 70: 2995-3007, 1992.
Barth et al., "Boron Neutron Capture Therapy of Brain Tumors: An Emerging Therapeutic Modality," *Neurosurgery* 44: 433-450, 1999.
Barth et al., "Boron Neutron Capture Therapy of Cancer: Current Status and Future Prospects," *Clin. Cancer Res.* 11: 3987-4002, 2005.
Bonnett, "Photosensitizers of the Porphyrin and Phthalocyanine Series for Photodynamic Therapy," *Chem. Soc. Rev.* 24: 19-33, 1995.
Capala et al., "Accumulation of Boron in Malignant and Normal Cells Incubated in Vitro with Boronophenylalanine, Mercaptoborane or Boric Acid," *Radiat. Res.* 146: 554-560, 1996.

Elowitz et al., "Biodistribution of p-Boronophenylalanine in Patients with Glioblastoma Multiforme for Use in Boron Neutron Capture Therapy," *Neurosurgery* 42: 463-469, 1998.
Gupta et al., "Common Challenges and Problems in Clinical Trials of Boron Neutron Capture Therapy of Brain Tumors," *J. Neurooncol.* 62: 197-210, 2003.
Hodgkiss, "Use of 2-Nitroimidazoles as Bioreductive Markers for Tumour Hypoxia," *Anti-Cancer Drug Design* 13: 687-702, 1998.
Kageji et al., "Pharmacokinetics and Boron Uptake of BSH ($Na_2B_{12}H_{11}SH$) in Patients with Intracranial Tumors," *J. Neurooncol.* 33: 117-130, 1997.
Kahl et al., "Synthesis of Tetrakis-Carborane-Carboxylate Esters of 2,4-bis-($\alpha$, $\beta$-Dihydroxyethyl)-Deuteroporphyrin IX," *J. Chem. Soc., Chem. Commun.* 1769-1771, 1990.
Locher, "Biological Effects and Therapeutic Possibilities of Neutrons," *American Journal of Roentgenology and Radium Therapy* 36: 1-13, 1936.
Matsumura et al., "A New Boronated Porphyrin (STA-BX909) for Neutron Capture Therapy: An in Vitro Survival Assay and in Vivo Tissue Uptake Study," *Cancer Lett.* 141: 203-209, 1999.
Miura et al., "Preparation of Carboranyl Porphyrins for Boron Neutron Capture Therapy," *Tetrahedron Letters* 31: 2247-2250, 1990.
Pignol et al., "Selective Delivery of $^{10}$B to Soft Tissue Sarcoma Using $^{10}$B-L-Borophenylalanine for Boron Neutron Capture Therapy," *Br. J. Radiol.* 71: 320-323, 1998.
Sasai et al., "Fluorinated 2-Nitroimidazole Derivative Hypoxic Cell Radiosensitizers: Radiosensitizing Activities and Pharmacokinetics," *Int. J. Radiat. Oncol. Biol. Phys.* 29: 579-582, 1994.
Scobie et al., "Tumour-Targeted Boranes. 4. Synthesis of Nitroimidazole-Carboranes with Polyether-Isoxazole Links," *J. Org. Chem.* 59: 7008-7013, 1994.
Scobie et al., "Tumour-Targeted Boranes. Part 3. Synthesis of Carbamate-Linked Nitroimidazolyl Carboranes Designed for Boron Neutron Capture Therapy of Cancer," *J. Chem. Soc., Perkin Trans.* 1 2059-2063, 1994.
Soloway et al., "The Chemistry of Neutron Capture Therapy," *Chem. Rev.* 98: 1515-1562, 1998.
Sugie et al., "Reevaluation of the Radiosensitizing Effects of Sanazole and Nimorazole in Vitro and in Vivo," *J. Radiat. Res.* 46: 453-459, 2005.
Swenson et al., "Synthesis and Evaluation of a Boronated Nitroimidazole for Boron Neutron Capture Therapy," *J. Med. Chem.* 39: 1540-1544, 1996.
Tolpin et al., "Synthesis and Chemistry of Mercaptoundecahydro-closo-dodecaborate (2-)," *Inorganic Chemistry* 17: 2867-2873, 1978.

(Continued)

*Primary Examiner*—D L Jones
(74) *Attorney, Agent, or Firm*—Clark & Elbing LLP

(57) ABSTRACT

The invention features a class of 2-nitroimidazole compounds with a secondary basic nitrogen atom and a linker bearing one or more therapeutic agents, cytotoxic agents, detectable labels, or chelating groups. In particular, the invention provides 2-nitroimidazole compounds containing a cluster of boron atoms for use in boron neutron capture therapy (BNCT). The 2-nitroimidazole compounds can be used to treat hypoxic conditions, including, e.g., cancer, inflammation, and ischemia. The weakly basic 2-nitroimidazole compounds target to hypoxic tissue and provide increased tissue concentration overall.

38 Claims, No Drawings

OTHER PUBLICATIONS

Wood et al., "Uptake and Retention of Nitroimidazole-Carboranes Designed for Boron Neutron Capture Therapy in Experimental Murine Tumours: Detection by $^{11}$B Magnetic Resonance Spectroscopy," *International Journal of Radiation Biology* 70: 587-592, 1996.

Ali et al., "Metal Complexes as Photo- and Radiosensitizers," Chem. Rev. 99:2379-2450.

Bormans et al., "Synthesis, Radio-LC-MS Analysis and Biodistribution in Mice of $^{99m}$Tc-NIM-BAT," J. Label. Compds Radiopharm. 46:575-585, 2003.

Papadopoulou et al., "Synthesis of Novel 2-Nitroimidazole-Tethered Tricyclic Quinolines, Bearing a Second Heteroatom, and their in Vitro Evaluation as Hypoxia-Selective Cytotoxins and Radiosensitizers," Bioorg. Med. Chem. Letters 14:1523-1525, 2004.

Papadopoulou et al., "Synthesis of Novel 2-Nitroimidazole-Spermidine Derivative as a Tumor-Targeted Hypoxia-Selective Cytotoxin," Bioorg. Med. Chem. Letters 14:1519-1522, 2004.

Supplementary European Search Report from EP 07 87 1243, dated Nov. 23, 2009.

Ali et al., "Metal complexes as photo- and radiosensitizers," *Chem. Rev.* 99:2379-2450, 1999.

* cited by examiner

HYPOXIA-SELECTIVE, WEAKLY BASIC 2-NITROIMIDAZOLE DELIVERY AGENTS AND METHODS OF USE THEREOF

This invention was made with Government support from the National Institutes of Health under grant number R41CA093124 awarded by the National Institutes of Health. The Government has certain rights in this invention.

FIELD OF THE INVENTION

This invention relates to a class of 2-nitroimidazole compounds, most preferably those bearing a cluster of boron atoms for boron neutron capture therapy (BNCT). The 2-nitroimidazole compounds can be used to treat or prevent hypoxic conditions, e.g., cancer, inflammation, and ischemia. The boronated 2-nitroimidazole compounds contain a secondary basic nitrogen atom that targets the compounds to hypoxic tissue, such as tumor tissue, thereby providing greater delivery of boron to hypoxic tissues than achieved by currently available boron delivery agents, such as disodium mercapto-closo-dodecaborate (BSH) and L-4-dihydroxy-borylphenylalanine (BPA). Thus, the compounds of the invention can be used to target and destroy hypoxic tissue, e.g., solid tumors, that possess a significant hypoxic fraction using neutron irradiation.

BACKGROUND OF THE INVENTION

Boron neutron capture therapy (BNCT) is a unique tumor cell targeting therapy (Soloway et al, Chem. Rev. 98:1515-1562, 1998; Barth et al., Clinical Res. 11:3987-4002, 2005). It is one of the binary cancer treatment systems that are based on the selective accumulation of boron-10 ($^{10}B$) in tumors followed by irradiation with a neutron source. The selective accumulation of $^{10}B$ in tumors and the subsequent capture of an epithermal neutron by a $^{10}B$ atom, which produces an α-particle ($He^{2+}$) and a lithium nucleus ($^{7}Li^{+}$) ejected in opposite directions within the tumor mass, make BNCT an attractive therapy for targeting tumors. The average track of these densely ionizing particles is approximately 14 μm, about the diameter of one cell, so that the killing of tumor cells is highly efficient (see Barth et al., Cancer 70:2995 3007, 1992; Barth et al., Neurosurg. 44:433 451, 1999; Soloway et al., J. Neurooncol. 33:9-18, 1997; and Soloway et al., 1998, supra). This promising radiation therapy requires the administration of tumor-seeking compounds containing $^{10}B$ atoms that concentrate preferentially in tumor cells prior to irradiation with suitable low energy neutron beams. This binary modality is a highly attractive cancer therapy in that neither the thermal neutrons nor the boron carrier molecule has significant cytotoxic effect alone, but in combination they produce highly radiobiologically effective particles. The alpha particle and Li ion that are released as fission products when a thermal neutron is absorbed by a $^{10}B$ atom have high linear energy transfer (LET) and a range similar to the dimensions of a mammalian cell. Thus, the absorbed dose, which is potent, is confined to cells adjacent to the boron atoms. The potential exists, therefore, to destroy tumor cells by radiosurgery at the microscopic level while sparing normal tissue in the vicinity of the tumor. BNCT is especially attractive for malignant brain tumors because it targets and destroys malignant cells but spares normal cells, thus preventing undesirable side effects common in standard chemo- or radiotherapy.

In recent years, several research groups have developed a variety of $^{10}B$ carriers, including porphyrin derivatives with improved tumor selectivity over prior boron neutron capture agents, such as disodium mercapto-closo-dodecaborate (BSH) and L-4-dihydroxy-borylphenylalanine (BPA). Porphyrin derivatives are currently being tested in clinical trials in the U.S., Europe, and Japan for the treatment of patients with glioblastomas and melanomas (see, e.g., Bonnett et al., Chem. Soc. Rev. 24:19-33, 1995; Kageji et al., J. Neurooncol. 33:117-130, 1997; Pignol et al., Br. J. Radiol. 71:320-323, 1998; Elowitz et al., Neurosurgery 42:463-469, 1998). Although BSH and BPA have been shown to be safe and efficacious in animal models, several problems remain. For instance, BSH is sensitive to air-oxidation (Tolpin et al., Inorg. Chem. 17:2867-2873, 1978) and both BSH and BPA have low retention times in tissues and only moderate selectivity for tumor cells (Capala et al., Radiation Res. 146:554-560, 1996). At present, clinical progress is stalled due to the absence of effective boron delivery agents that target tumor cells with high selectivity. Obviously, the ultimate success of BNCT will be dependent upon whether adequate concentrations of boron neutron capture agents and low-energy neutrons can be selectively and effectively delivered to tumor cells.

Hypoxic tumor cells that comprise up to 50% of the mass of viable cells in human tumors pose a special impediment to effective radio- and chemotherapy. In particular, hypoxic cells are highly radio-resistant and capable of proliferation following radiation treatment. If boron containing therapeutics that interact with epithermal neutrons are not delivered to hypoxic sites in tumors it can be anticipated that the effectiveness of BCNT will be significantly compromised. In principal, BNCT is well suited to treating poorly oxygenated tumors since reduced radio-sensitivity in the absence of oxygen is less pronounced for high LET radiations, yet the effectiveness of BNCT therapy is dependent on delivery of the agent carrying the $^{10}B$ atom to the tumor site.

2-nitroimidazoles readily penetrate tumors and can reach intratumor concentrations approaching 1 mM. As Varghese et al. showed in 1976 (Scobie et al., 1994), 2-nitroimidazoles also undergo nitroreductive activation under hypoxic conditions to yield electrophilic species that form adducts with cellular macromolecules, such as DNA and proteins. These adducts are retained in hypoxic cells and represent a useful targeting mechanism. In fact, carboranes have been linked to nitroimidazoles (Wood et al., 1996; Swenson et al., 1996) in attempts to target boron selectively to the hypoxic regions of tumors, but these boron delivery agents suffered greatly from poor water solubility. Thus, there remains a need for highly effective reagents for use in treating tumor tissue.

SUMMARY OF THE INVENTION

This invention is related to a novel class of 2-nitroimidazole delivery agents with a secondary nitrogen atom that serves as a weakly basic functional group. The 2-nitroimidazole delivery agents of the invention can include one or more of a therapeutic agent, a cytotoxic agent (e.g., a boron cluster), a diagnostic agent, or a chelating agent. The secondary nitrogen atom of the 2-nitroimidazole delivery agent enhances significantly the water solubility and uptake of the delivery agent into tissues experiencing microenvironments that include gradients of pH and hypoxia. We have synthesized several delivery agents carrying $^{10}B$ for BNCT with a view to using them alone or in combination with existing boron carriers to treat solid tumors. Furthermore, these compounds labeled with [F18] or [F19] or other detectable labels may be used as diagnostics for hypoxia by means of PET or MRS/MRI, respectively.

A first aspect of the invention features a compound having the structure of formula I

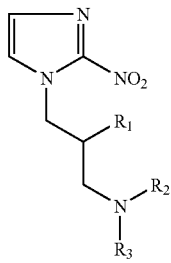

in which R1 is a halogen (e.g., fluorine (F), chlorine (Cl), bromine (Br), iodine (I), or astatine (At)), positron emitting radionuclide (e.g., [11C], [13N], [15O], [18F], [52Fe], [55Co], [61Cu], [62Cu], [64Cu], [62Zn], [63Zn], [70As], [71As], [74As], [76Br], [79Br], [82Rb], [86Y], [89Zr], [110In], [120I], [124I], [122Xe], [94mTc], [94Tc], or [99mTc]), non-metal (e.g., [31P] or [13C]), lower alkyl substituted to contain a halogen, lower alkyl substituted to contain a positron emitting radionuclide, lower alkyl substituted to contain a non-metal, tosylate, mesylate, tryflate, hydrogen, or hydroxyl; and R2 and R3 are independently selected from a hydrogen, lower alkyl, allyl, alkenyl, alkynyl, hydroxyalkyl, heteroalkyl, polyether, or polyether with a terminal heteroatom (e.g., a nitrogen, oxygen, and sulfur atom), such that at least one of R2 or R3 further contains a therapeutic agent (e.g., antibiotic, a supplementary potentiating agent, an hormonal agonist or antagonist, an apoptotic agent, and an immunomodulator), cytotoxic agent (e.g., a radiosensitizer (e.g., a boron cluster, such as decaborane, dodecaborane, closo-1,2-carborane, or methyl-o-carborane), an alkylating agent, an antineoplastic agent, an antiproliferative agent, an antimetabolic agent, a tubulin inhibitor, and a topoisomerase I or II inhibitor; the cytotoxic agent can also be selected from camptothecin, homocamptothecin, colchicine, combretastatin, dolistatin, doxorubicin, methotrexate, podophyllotoxin, rhizoxin, rhizoxin D, a taxol, paclitaxol, cisplatin, CC1065, a maytansinoid, and derivatives and analogs thereof), detectable label (e.g., a radiolabel), or chelating group (e.g., an ininocarboxylic reactive group, polyaminopolycarboxylic reactive group, diethylenetriaminepentaacetic acid (DTPA), or 1,4,7,10-tetraazacyclododecane-1,4,7,10-tetraacetic acid (DOTA)). Alternatively, R2 and R3 of the compound are linked to form a five-, six-, or seven-membered heterocyclic ring containing at least one nitrogen atom (e.g., at least 2, 3, or 4 nitrogen atoms), in which the heterocyclic ring contains a therapeutic agent, cytotoxic agent, detectable label, or chelating group.

In an embodiment of the first aspect of the invention, the compound has the structure of formula II-XI. In another embodiment, R1 is a halogen (e.g., [F18] or [F19]) or a non-metal. In another embodiment, R2 and R3 contain a therapeutic or a cytotoxic agent; the therapeutic or cytotoxic agents can be the same or different. In other embodiments, either R2 or R3 can be a polyether that terminates with a boron cluster. In yet another embodiment, the therapeutic agent, cytotoxic agent, detectable label, or chelating group is attached to the compound by an enzymatically cleavable bond. In another embodiment of the first aspect of the invention the therapeutic agent is covalently bonded to the compound through a heteroatom attached to a polyether (either R2 or R3 or both). The compound of the first aspect of the invention can be admixed with a pharmaceutically acceptable carrier or excipient or the compound can be provided in salt form with an anionic counterion (e.g., a halide).

A second aspect of the invention features a method of treating or preventing a hypoxic condition (e.g., cancer, such as glioblastoma, gliosarcoma, or melanoma tumor cells), inflammation, or ischemia) in a patient in need thereof by administering the compound of claim 1 to the patient. In an embodiment, R2 or R3 of the compound contains a boron cluster and the method involves the use of boron neutron capture therapy (BNCT) following the administration to the patient of an amount of the compound sufficient for selective uptake, retention, and damage to cells present in hypoxic tissue when the cells are irradiated by thermal neutrons. In another embodiment, the compound further contains a cytotoxic agent. The compound can be administered with a pharmaceutically acceptable carrier or excipient, or the compound can be provided in salt form with an anionic counterion (e.g., a halide).

A third aspect of the invention features a method for detecting hypoxic cells (e.g., cancer cells, such as glioblastoma, gliosarcoma, or melanoma cells) in normal, diseased normal, or malignant tissue in a mammal by a) administering to the mammal the compound of claim 1, in which the compound contains a radionuclide (e.g., [11C], [13N], [15O], [18F], [52Fe], [55Co], [61Cu], [62Cu], [64Cu], [67Cu], [67Ga], [68Ga], [62Zn], [63Zn], [70As], [71As], [74As], [76Br], [79Br], [82Rb], [86Y], [89Zr], [110In], [111In], [120I], [123I], [124I], [125I], [131I], [122Xe], [175Lu], [154Gd], [155Gd], [156Gd], [157Gd], [158Gd], [94mTc], [94Tc], or [99mTc]) at R1, and detecting any of the compound retained in the normal, diseased normal, or malignant tissue by non-invasive positron emission tomography (PET); or in which the compound contains a halogen or a non-metal at R1, and the detecting any of the compound retained in the normal, diseased normal, or malignant tissue by magnetic resonance spectroscopy (MRI) or magnetic resonance imaging (MRI). In a preferred embodiment, the radionuclide is [19F]. In another embodiment, R2 or R3 of the compound contains a therapeutic agent, cytotoxic agent (e.g., radiosensitizer, such as a boron cluster (e.g., decaborane, dodecaborane, closo-1, 2-carborane, or methyl-o-carborane)), an alkylating agent, an antineoplastic agent, an antiproliferative agent, an antimetabolic agent, a tubulin inhibitor, or a topoisomerase I or II inhibitor), detectable label (e.g., [11C], [13N], [15O], [18F], [52Fe], [55Co], [61Cu], [62Cu], [64Cu], [67Cu], [67Ga], [68Ga], [62Zn], [63Zn], [70As], [71As], [74As], [76Br], [79Br], [82Rb], [86Y], [89Zr], [110In], [111In], [120I], [123I], [125I], [131I], [122Xe], [175Lu], [154Gd], [155Gd], [156Gd], [157Gd], [158Gd], [94mTc], [94Tc], or [99mTc]), or a chelating group. In yet another embodiment, R2 and R3 of the compound contain a cytotoxic agent, detectable label, or chelating group. In another embodiment, the compound has the structure of any one of formula II-XI. The method involves administering to the patient an amount of the compound sufficient for selective uptake, retention, and detection of hypoxic cells. The compound can be administered with a pharmaceutically acceptable carrier or excipient, or in a salt form with an anionic counterion (e.g., a halide).

In other embodiments of the method of the third aspect of the invention, the compound contains a halogen (e.g., [19F]) or a non-metal (e.g., [31P] or [13C]).

We have synthesized a number of boronated 2-nitroimidazole analogues (Chart 1) as boron delivery agents for BNCT. The conjugated closo-carboranyl [$C_2B_{10}H_{10}$] group was introduced through the reaction of the bisacetonitrile adduct of decaborane ($B_{10}H_{12}$-2$CH_3CN$) and 5-hexyn-1-tosylate to give an intermediate compound, which was then coupled with 2-nitroimidazole to afford the desired products. The boron-containing compounds were identified by $^1$H, $^{13}$CNMR, and MALDI-TOF MS.

In the generic descriptions of compounds of this invention, the number of atoms of a particular type in a substituent group is generally given as a range, e.g., an alkyl group containing from 1 to 7 carbon atoms or $C_{1-7}$ alkyl. Reference to such a range is intended to include specific references to groups having each of the integer number of atoms within the specified range. For example, an alkyl group from 1 to 7 carbon atoms includes each of $C_1$, $C_2$, $C_3$, $C_4$, $C_5$, $C_6$, and $C_7$. A $C_{1-7}$ heteroalkyl, for example, includes from 1 to 6 carbon atoms in addition to one or more heteroatoms. Other numbers of atoms and other types of atoms may be indicated in a similar manner.

By "allyl" is meant an alkene hydrocarbon group with the formula $H_2C=CH-CH_2-R$.

By "alkaryl" is meant an alkyl substituted by an aryl group (e.g., benzyl, phenethyl, or 3,4-dichlorophenethyl) having from 7 to 14 carbon atoms.

By "alkenyl" is meant a branched or unbranched hydrocarbon group containing one or more double bonds and having from 2 to 24 carbon atoms. An alkenyl may optionally include monocyclic or polycyclic rings, in which each ring desirably has from three to six members. The alkenyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, carboxyalkyl, and carboxyl groups. Alkenyls include, without limitation, vinyl; allyl; 2-cyclopropyl-1-ethenyl; 1-propenyl; 1-butenyl; 2-butenyl; 3-butenyl; 2-methyl-1-propenyl; 2-methyl-2-propenyl; 1-pentenyl; 2-pentenyl; 3-pentenyl; 4-pentenyl; 3-methyl-1-butenyl; 3-methyl-2-butenyl; 3-methyl-3-butenyl; 2-methyl-1-butenyl; 2-methyl-2-butenyl; 2-methyl-3-butenyl; 2-ethyl-2-propenyl; 1-methyl-1-butenyl; 1-methyl-2-butenyl; 1-methyl-3-butenyl; 2-methyl-2-pentenyl; 3-methyl-2-pentenyl; 4-methyl-2-pentenyl; 2-methyl-3-pentenyl; 3-methyl-3-pentenyl; 4-methyl-3-pentenyl; 2-methyl-4-pentenyl; 3-methyl-4-pentenyl; 1,2-dimethyl-1-propenyl; 1,2-dimethyl-1-butenyl; 1,3-dimethyl-1-butenyl; 1,2-dimethyl-2-butenyl; 1,1-dimethyl-2-butenyl; 2,3-dimethyl-2-butenyl; 2,3-dimethyl-3-butenyl; 1,3-dimethyl-3-butenyl; 1,1-dimethyl-3-butenyl and 2,2-dimethyl-3-butenyl.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups. The $C_{1-24}$ alkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{1-24}$ alkyls include, without limitation, methyl; ethyl; n-propyl; isopropyl; cyclopropyl; cyclopropylmethyl; cyclopropylethyl; n-butyl; iso-butyl; sec-butyl; tert-butyl; cyclobutyl; cyclobutylmethyl; cyclobutylethyl; n-pentyl; cyclopentyl; cyclopentylmethyl; cyclopentylethyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; cyclohexyl; octyl; decyl; eicosyl; tetracosyl; and the like. Preferred alkyl groups herein are "lower alkyl groups," which can contain from 1 to 15 carbons. More preferably, lower alkyl groups contain only 1 to 5 carbons, inclusive.

By "alkheterocyclyl" is meant an alkyl substituted heterocyclic group having from 7 to 14 carbon atoms in addition to one or more heteroatoms (e.g., 3-furanylmethyl, 2-furanylmethyl, 3-tetrahydrofuranylmethyl, or 2-tetrahydrofuranylmethyl).

By "alkynyl" is meant a branched or unbranched hydrocarbon group containing one or more triple bonds and having from 2 to 24 carbon atoms. An alkynyl may optionally include monocyclic, bicyclic, or tricyclic rings, in which each ring desirably has five or six members. The alkynyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. Alkynyls include, without limitation, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, 5-hexynyl; 1-methyl-2-propynyl; 1-methyl-2-butynyl; 1-methyl-3-butynyl; 2-methyl-3-butynyl; 1,2-dimethyl-3-butynyl; 2,2-dimethyl-3-butynyl; 1-methyl-2-pentynyl; 2-methyl-3-pentynyl; 1-methyl-4-pentynyl; 2-methyl-4-pentynyl; and 3-methyl-4-pentynyl.

By "analog" is meant a molecule that differs from, but is structurally, functionally, and/or chemically related to the reference molecule. The analog may retain the essential properties, functions, or structures of the reference molecule. Most preferably, the analog retains at least one biological function of the reference molecule. Generally, differences are limited so that the structure or sequence of the reference molecule and the analog are similar overall.

By "aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary subsituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "chelating agent" is meant a molecule that forms multiple chemical bonds with a single metal atom. Prior to forming the bonds, the chelating agent has more than one pair of unshared electrons. The bonds are formed by sharing pairs of electrons with the metal atom.

Chelating agents include, for example, an iminodicarboxylic group or a polyaminopolycarboxylic group. Chelating agents may be attached to a 2-nitroimidazole compound of the invention using the methods generally described in Liu et al., *Bioconjugate Chem.* 12(4):653, 2001; Alter et al., U.S. Pat. No. 5,753,627; and PCT Publication No. WO 91/01144; each of which are hereby incorporated by reference). A 2-nitroimidazole compound of the invention may be complexed, through its attached chelating agent, to a detectable label, thereby resulting in a compound that is indirectly labeled. Similarly, cytotoxic or therapeutic agents, may also be attached via a chelating group to a 2-nitroimidazole compound of the invention.

By "coupled" is meant the characteristic of a first molecule being joined to a second molecule by a covalent bond or through noncovalent intermolecular attraction.

By "cytotoxic agent" is meant any naturally-occurring, modified, or synthetic compound that is toxic to tumor cells. Such agents are useful in the treatment of neoplasms, and in the treatment of other symptoms or diseases characterized by cell proliferation or a hyperactive cell population. Cytotoxic agents include, but are not limited to, alkylating agents, antibiotics, antimetabolites, tubulin inhibitors, topoisomerase I and II inhibitors, hormonal agonists or antagonists, or immunomodulators. Cytotoxic agents may be cytotoxic when activated by light or infrared (Photofrin, IR dyes; Nat. Biotechnol. 19(4):327-331, 2001), may operate through other mechanistic pathways, or be supplementary potentiating agents.

By "detectable label" is meant any type of label which, when attached to a 2-nitroimidazole compound of the invention, renders the compound detectable. A detectable label may be toxic or non-toxic, and may have one or more of the following attributes, without restriction: fluorescence (Kiefer et al., WO 9740055), color, toxicity (e.g., radioactivity, e.g., a γ-emitting radionuclide, Auger-emitting radionuclide, β-emitting radionuclide, an α-emitting radionuclide, or a positron-emitting radionuclide), radiosensitivity, or photosensitivity. Although a detectable label may be directly attached to the compound of the invention, a detectable label may also be indirectly attached, for example, by being complexed with a chelating group that is attached (e.g., linked via a covalent bond or indirectly linked) to a 2-nitroimidazole compound of the invention. A detectable label may also be indirectly attached to a 2-nitroimidazole compound of the invention by the ability of the label to be specifically bound by a second molecule. One example of this type of an indirectly attached label is a biotin label that can be specifically bound by the second molecule, streptavidin. The second molecule may also be linked to a moiety that allows neutron capture (e.g., a boron cage as described in, for example, Kahl et al., Proc. Natl. Acad. Sci. USA 87:7265-7269, 1990).

A detectable label may also be a metal ion from heavy elements or rare earth ions, such as $Gd^{3+}$, $Fe^{3+}$, $Mn^{3+}$, or $Cr^{2+}$ (see, for example, Invest. Radiol. 33(10):752-761, 1998). Radioactive detectable labels include, e.g., radioactive iodine labels (e.g., $^{122}I$, $^{123}I$, $^{124}I$, $^{125}I$, or $^{131}I$). Non-radioactive detectable labels can also be attached to 2-nitroimidazole compounds of the invention.

Preferred examples of detectable labels that may be toxic to cells include ricin, diptheria toxin, and radioactive detectable labels (e.g., $^{122}I$, $^{123}I$, $^{124}I$, $^{125}I$, $^{131}I$, $^{177}Lu$, $^{64}Cu$, $^{67}Cu$, $^{153}Sm$, $^{166}Ho$, $^{186}Re$, $^{188}Re$, $^{211}At$, $^{212}Bi$, $^{225}Ac$, $^{67}Ga$, $^{68}Ga$, $^{75}Br$, $^{76}Br$, $^{77}Br$, $^{117m}Sn$, $^{47}Sc$, $^{109}Pd$, $^{89}Sr$, $^{159}Gd$, $^{149}Pm$, $^{142}Pr$, $^{111}Ag$, $^{165}Dy$, $^{213}Bi$, $^{111}In$, $^{114m}In$, $^{201}Ti$, $^{195m}Pt$, $^{193}Pt$, $^{86}Y$ and $^{90}Y$). These compounds, and others described herein may be directly or indirectly attached to 2-nitroimidazole compounds of the invention. A toxic detectable label may also be a chemotherapeutic agent (e.g., camptothecins, homocamptothecins, 5-fluorouracil or adriamycin), or may be a radiosensitizing agent (e.g., Taxol, gemcitabine, fluoropyrimidine, metronitozil, or the deoxycytidine analog 2',2'-difluoro-2'-deoxycytidine (dFdCyd)) to which is directly or indirectly attached a 2-nitroimidazole compound of the present invention.

A detectable label, when coupled to a 2-nitroimidazole compound of the invention, emits a signal that can be detected by a signal transducing machine. In some cases, the detectable label can emit a signal spontaneously, such as when the detectable label is a radionuclide. In other cases the detectable label emits a signal as a result of being stimulated by an external field such as when the detectable label is a relaxivity metal. Examples of signals include, without limitation, gamma rays, X-rays, visible light, infrared energy, and radiowaves. Examples of signal transducing machines include, without limitation, gamma cameras including SPECT/CT devices, PET scanners, fluorimeters, and Magnetic Resonance Imaging (MRI) and Magnetic Resonance Spectroscopy (MRS) machines.

By "fluoroalkyl" is meant an alkyl group that is substituted with a fluorine.

By "halide" is meant bromine, chlorine, iodine, or fluorine.

By "heterocyclyl" is meant a stable 5- to 7-membered monocyclic or 7- to 14-membered bicyclic heterocyclic ring which is saturated partially unsaturated or unsaturated (aromatic), and which consists of 2 to 6 carbon atoms and 1, 2, 3 or 4 heteroatoms independently selected from the group consisting of N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "heteroalkyl" is meant a branched or unbranched alkyl, alkenyl, or alkynyl group having from 1 to 24 carbon atoms in addition to 1, 2, 3, 4, or more heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, hydroxyalkyl, carboxyalkyl, and carboxyl groups.

The term "hydroxyalkyl" refers to alkyl groups containing a hydroxyl group.

The term "mesylate" refers to esters formed when a hydroxyl group reacts with methane sulfonyl choride, but may include methane sulfonyl chlorides in which the methane moiety is substituted with alkyl, halide, ester, ether or cyano groups or the like.

By "polyether" is meant a group in which the repeating unit contains two carbon atoms linked by an oxygen atom ($R_1$—$CH_2$—$CH_2$—O—$CH_2$—$CH_2$—$R_2$)$_n$, where n=1-15. The polyether can be terminated with a heteroatom, e.g., nitrogen, oxygen, or sulfur.

The term "tosylate" refers to esters formed when a hydroxyl group reacts with p-toluene sulfonyl chloride, but may include toluene sulfonyl chlorides in which the toluene moiety is substituted with alkyl, halide, ester, ether or cyano groups or the like.

By "treating or preventing cancer" is meant causing a reduction in the size of a tumor or number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. In a desired embodiment, the percent of tumor or cancerous cells surviving treatment with a 2-nitroimidazole compound of the invention (e.g., a boronated 2-nitroimidazole compound) is at least 20, 40, 60, 80, or 100% lower than the initial number of tumor or cancerous cells, as measured using any standard assay. Desirably, the decrease in the number of tumor or cancerous cells induced by administration of a 2-nitroimidazole compound of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or number of cancerous cells as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after at least 5, 10, 15, or 20 years.

The term "tryflate" refers to esters formed when a hydroxyl group reacts with trifluoromethane sulfonyl anhydride.

By "within the framework of the ring" is meant the incorporation of an atom or at least one atom of a group within the contiguous atoms of a ring structure.

Examples are presented in terms of fluorinated 2-nitroimidazoles but it is known to those skilled in the art that, in the case of PET, compounds of the invention may be labeled with any positron emitting nuclide, including, e.g., [76Br] and [124I].

It is to be understood that the compounds of the invention may be used for PET, MRS, and MRI detection of tissue hypoxia and that the advantages of reagents that incorporate a weakly basic moiety accrue to [18]PET, [19F]MRS and [19F]MRI. It is also to be understood that the inventors recognize that increasing the number of halogen atoms, such as [19F], by procedures well known to those skilled in the art of chemical synthesis will increase detection sensitivity for MRS/MRI in a manner that increases with the square of the number of halogen atoms present in the compounds.

It is to be understood that intravenous administration is the preferred route for embodiments related to the treatment or prevention of hypoxic tissues and for PET studies (using, e.g., [18F]), but that intravenous or oral administration can be used to administer the 2-nitroimidazole compounds of the invention when used in [19]MRS or [19F]MRI analyses of tissue hypoxia.

Other features and advantages of the invention will be apparent from the following description of the preferred embodiments thereof, and from the claims.

DETAILED DESCRIPTION

The invention is directed to the synthesis and use of 2-nitroimidazole compounds that contain a secondary nitrogen that serves as a weakly basic functional group for improving water solubility and uptake of the compounds into hypoxic tissues, such as tumor cells. The 2-nitroimidazole compounds contain one or more of a therapeutic agent, cytotoxic agent, detectable label, or chelating group. In preferred embodiments, the 2-nitroimidazole compounds contain one or more boron clusters or a boron cluster and a cytotoxic agent. In this regard, the invention provides an improved method for linking the carboranyl group by a carbon-carbon or polyether linkage to the 2-nitroimidazole moiety. The boronated 2-nitroimidazole compounds generally correspond to general formula I.

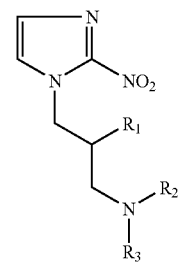

I

The novel 2-nitroimidazole compounds, which incorporating weakly basic moieties (pKa about 8 or greater) and one or more of a therapeutic agent, cytotoxic agent (e.g., a boron cluster), detectable label (e.g., a halogen, a positron-emitting radionuclide, or a non-metal), or chelating group, facilitate the non-invasive detection and treatment of hypoxic tissue. In particular, the 2-nitroimidazole compounds of the invention can be used to detect hypoxic tissue (e.g., tumor tissue) prior to therapeutic intervention, which, in turn, allows for the selection of patients for hypoxia-based therapeutic interventions in an effective and timely manner. More importantly, the 2-nitroimidazole compounds of the invention can be used for therapeutic interventions in diseased normal and malignant tissue. In particular, the 2-nitroimidazole compounds of the invention are useful for treating or prevention hypoxic conditions, such as cancer, present in, e.g., tissues of the skin (e.g., squamous cell carcinoma, basal cell carcinoma, or melanoma), breast, colorectal organs, urogenital organs (e.g., prostate, testicles, ovaries, bladder), brain and nervous system, head and neck, pancreas, lung, liver (e.g., hepatoma), kidney, gastrointestinal tract, heart, eyes, stomach, bone, endocrine system (e.g., thyroid and pituitary tumors), and lymphatic system (e.g., Hodgkin's and non-Hodgkin's lymphomas). The hypoxic conditions to be treated can also result from ischemia (e.g., as a result of stroke), inflammation, and wound healing.

The invention provides compounds for the non-invasive detection of both chronic and acute hypoxia using PET, MRS, and MRI, and for the treatment or prevention of hypoxic tissues or conditions. The compounds efficiently incorporate into chronic and acute hypoxic tissues. The 2-nitroimidazole compounds of the invention can be used in two ways. First, the level of tissue hypoxia prior to therapy can be assessed, which allows for the selection of patients who may benefit from a hypoxia-based intervention. The level of tissue hypoxia following therapy can also be assessed, which allows for the detection of changes in tissue hypoxia in response to therapeutic interventions. Second, the 2-nitroimidazole compounds of the invention can be used to treat or prevent a hypoxic condition (e.g., cancer, inflammation, and ischemia). The 2-nitroimidazole compounds of the invention can be used in conjuction with ionizing radiation, hyperthermia, hypoxic cell radiosensitizers, bioreductive cytotoxins, anti-inflammatory agents, or growth factor inhibitors.

We have successfully synthesized a number of closo-carboranes containing compounds (see Formulas II, III, IV, and V below). Their structures were confirmed by $^1$H, $^{13}$CNMD and MALDI-TOF MS.

Chart 1:

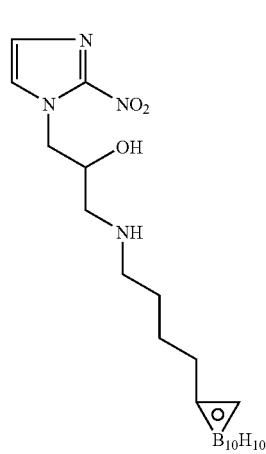

II

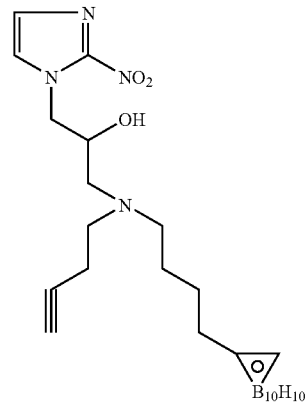

III

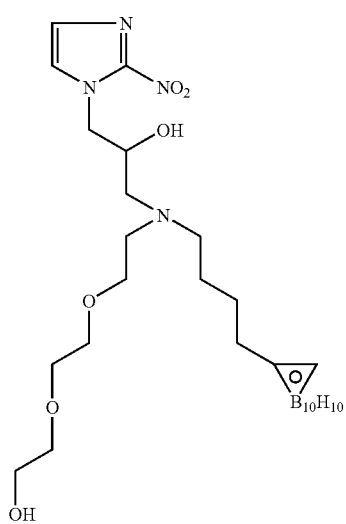

IV

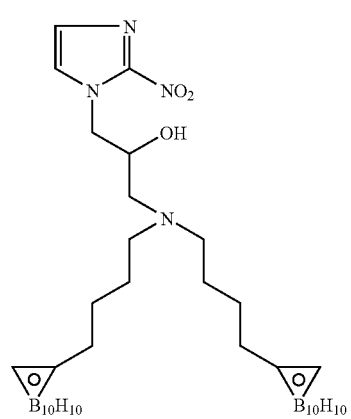

V

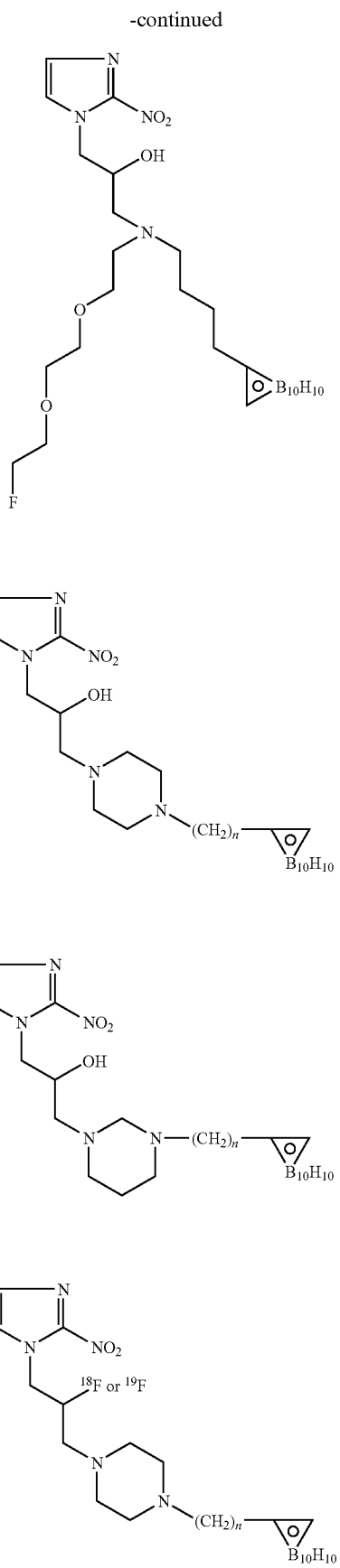

The carboranyl-containing 2-nitroimidazole compounds of the invention can be used to treat, prevent, and detect, e.g., tumor cells, in patients. In preferred embodiments, the treatment or prevention of cancer using the boronated 2-nitroimidazole compounds involves the use of boron neutron capture therapy (BNCT). Accordingly, the invention includes a method for delivering an effective amount of a neutron capture agent to tumor cells, which involves contacting the tumor cells with a carboranyl-containing 2-nitroimidazole compound of the invention. In vivo, the method includes administering the carboranyl-containing 2-nitroimidazole compound to a patient, which is then selectively taken up by the tumor cells. To be effective in BNCT, the amount of boronated 2-nitroimidazole compound taken up by the tumor cells is an amount sufficient for cytotoxicity when the tumor cells are irradiated by thermal neutrons. Preferably, the tumor cells are brain tumor or melanoma cells, but can include any of a number of tumor cells, including without limitation tumor cells present in skin (e.g., squamous cell carcinoma, basal cell carcinoma, or melanoma), breast, colon/rectum, prostate, brain and nervous system, head and neck, testicles, ovaries, pancreas, lung, liver (e.g., hepatoma), kidney, bladder, gastrointestinal tract, bone, endocrine system (e.g., thyroid and pituitary tumors), and lymphatic system (e.g., Hodgkin's and non-Hodgkin's lymphomas) cancers. Cancers of the nervous-system include, for example, astrocytoma, oligodendroglioma, meningioma, neurofibroma, glioblastoma, gliosarcoma, ependymoma, Schwannoma, neurofibrosarcoma, neuroblastoma, and medulloblastoma. Other types of cancers that can be treated using the methods of the invention include fibrosarcoma, neuroectodermal tumor, mesothelioma, epidermoid carcinoma, as well as any other cancers that form solid tumors. Preferred tumor cells are those which are found in microenvironments with a high pH gradient and low oxygenation (i.e., hypoxic tissues).

The present invention also includes compositions for use in detecting tumor cells that include an effective amount of a carboranyl-containing 2-nitroimidazole compound with F18 or F19 attachment for PET or MRS/MRI detection, respectively, for diagnosis and treatment of human cancer. The carboranyl-containing 2-nitroimidazole compound can be administered with a pharmaceutically acceptable carrier or excipient, or in a salt form (e.g., with anionic counterions, such as a halide). An effective amount for PET or MRS/MRI is an amount of a compound of the invention sufficient for selective uptake, retention, and detection of tumor cells, when using the compounds of the invention to detect tumor cells.

The present invention also includes compositions for use in BNCT that include an effective amount of a carboranyl-containing 2-nitroimidazole compound containing a cytotoxic moiety (e.g., a platinum (Pt) complex, a nitrogen mustard prodrug, etc) for further enhancement of tumor cell treatment when combined with a pharmaceutically acceptable carrier or excipient. An effective amount for BNCT is an amount of a compound of the invention sufficient for selective uptake, retention and damage to tumor cells when the tumor cells that have absorbed the compound are irradiated by thermal neutrons.

Schemes 1 through 6 describe the total synthesis of carboranyl compound II to VI. These 2-nitroimidazole compounds contain carbon-carbon, or carbon oxygen linkages between the carboranyl groups and 2-nitroimidazole moiety for increased chemical stability over existing drugs under in vitro and in vivo conditions. In addition, the high solubility of these new drugs in aqueous solution allows for their easy administration into the blood stream via, for example, a concentrated saline solution of the drug without the need for a co-solvent. In vitro and in vivo biological activities of the new drugs show that these new compounds are very promising drugs for BNCT, diagnosis, and cytotoxic treatment of hypoxic tumor cells.

Compounds of the Invention

The novel compounds provided herein are those defined by the structural formula (I).

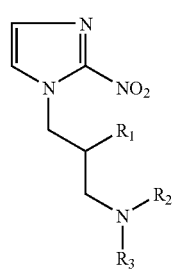

I in which R1 is a halogen (e.g., fluorine (F), chlorine (Cl), bromine (Br), iodine (I), or astatine (At)), positron emitting radionuclide (e.g., [11C], [13N], [15O], [18F], [52Fe], [55Co], [61Cu], [62Cu], [64Cu], [67Cu], [67Ga], [68Ga], [62Zn], [63Zn], [70As], [71As], [74As], [76Br], [79Br], [82Rb], [86Y], [89Zr], [110In], [111In], [120I], [123I], [124I], [125I], [131I], [122Xe], [175Lu], [154Gd], [155Gd], [156Gd], [157Gd], [158Gd], [94mTc], [94Tc], and [99mTc]), non-metal (e.g., [31P] and [13C]), lower alkyl substituted to contain a halogen, lower alkyl substituted to contain a positron emitting radionuclide, lower alkyl substituted to contain a non-metal, tosylate, mesylate, tryflate, hydrogen, or hydroxyl; and R2 and R3 are independently selected from a hydrogen, lower alkyl, allyl, alkenyl, alkynyl, hydroxyalkyl, heteroalkyl (e.g., a hydroxyether), polyether, or polyether with a terminal heteroatom (e.g., nitrogen, oxygen, or sulfur atom), in which at least one of R2 or R3 contains a therapeutic agent, cytotoxic agent, detectable label, or chelating group; or R2 and R3 or are linked to form a five-, six-, or seven-membered heterocyclic ring containing at least one nitrogen atom (e.g., at least 1, 2, 3, or 4 nitrogen atoms), wherein the heterocyclic ring contains a therapeutic agent, cytotoxic agent, detectable label, or chelating group.

Preferably, R2 and R3 are linked to form a five-, six-, or seven-membered heterocycyclic ring that has at least one nitrogen atom, but excludes groups in the ring that decrease basicity, such as O, S, or N-acyl. At least one N atom in structure (I) may be in salt form with anionic counterions including, but not limited to, a halide. In the case of multiple N atoms, at least one N may be substituted with a lower alkyl, hydroxyalkyl or fluoroalkyl group.

Radiolabeled compounds of the invention are useful compositions for imaging, detection, diagnosis, and treatment of disease (e.g., the presence of a solid tumor) in a subject. Numerous radiolabels may be used to generate radiolabeled compounds that are useful in imaging, detection, diagnosis, and treatment. For example, a non-limiting list of radiolabels that may be used to generate radiolabeled compounds include [11C], [13N], [15O], [18F], [52Fe], [55Co], [61Cu], [62Cu], [64Cu], [67Cu], [67Ga], [68Ga], [62Zn], [63Zn], [70As], [71As], [74As], [76Br], [79Br], [82Rb], [86Y], [89Zr], [110In], [111In], [120I], [123I], [124I], [125I], [131I], [122Xe], [175Lu], [154Gd], [155Gd], [156Gd], [157Gd], [158Gd], [94mTc], [94Tc], and [99mTc]). Particularly preferred radiolabels include [18F], [64Cu], [76Br], [124I], and mixtures thereof.

Therapeutic or Cytotoxic Agents Coupled to Compounds of the Invention

The 2-nitroimidazole compounds of the invention can be coupled to a therapeutic or cytotoxic agent. Examples of therapeutic and cytotoxic agents include, e.g., antineoplastic agents such as: Acivicin; Aclarubicin; Acodazole Hydrochloride; Acronine; Adozelesin; Adriamycin; Aldesleukin; Altretamine; Ambomycin; A. metantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Camptothecin; Caracemide; Carbetimer; Carboplatin; Carmustine; Carubicin Hydrochloride; Carzelesin; Cedefingol; Chlorambucil; Cirolemycin; Cisplatin; Cladribine; Combretestatin A-4; Crisnatol Mesylate; Cyclophosphamide; Cytarabine; Dacarbazine; DACA (N-[2-(Dimethyl-amino) ethyl]acridine-4-carboxamide); Dactinomycin; Daunorubicin Hydrochloride; Daunomycin; Decitabine; Dexormaplatin; Dezaguanine; Dezaguanine Mesylate; Diaziquone; Docetaxel; Dolasatins; Doxorubicin; Doxorubicin Hydrochloride; Droloxifene; Droloxifene Citrate; Dromostanolone Propionate; Duazomycin; Edatrexate; Eflornithine Hydrochloride; Ellipticine; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; Gemcitabine; Gemcitabine Hydrochloride; Gold Au 198; Homocamptothecin; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride;

Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; PeploycinSulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Rhizoxin; Rhizoxin D; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2' Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-Nnitrosourea (MNU); N,N'-Bis(2-chloroethyl)-N-nitrosourea (BCNU); N-(2-chloroethyl)-N' cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl) ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); or 2-chlorodeoxyadenosine (2-Cda).

Other anti-neoplastic compounds that can be coupled to 2-nitroimidazole compounds of the invention include, but are not limited to, 20-pi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e.g., 10-hydroxycamptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; episteride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; merbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+ myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of hormonal agonists include the following: leuprolide+estrogen+progesterone, leuprorelin, nafarelin, thyroid stimulating hormone, triptorelin, lanreotide, vapreotide, thrombopoietin, thrombopoietin mimetic, interleukins, and estrogen agonists.

Examples of hormonal antagonists include the following: abiraterone, antarelix, antiandrogen, antiestrogen, atamestane, cetrorelix, finasteride, ganirelix, human chorionic gonadotropin monoclonal antibody, onapristone, osaterone, superactive vasoactive intestinal peptide antagonist, tropisetron, and zanoterone.

Examples of apoptotic agents include the following: aclarubicin, apoptosis gene modulators, apoptosis regulators, arginine deaminase, clotrimazole, curacin A, etoposide, gemcitabine, ras inhibitors, ras-GAP inhibitor, and topotecan.

2-nitroimidazole compounds of the invention containing a therapeutic or cytotoxic agent can also be prepared by coupling the 2-nitroimidazole compound to an antiproliferative agent, for example piritrexim isothionate. Alternatively, 2-nitroimidazole compounds of the invention can also be coupled to an antiprostatic hypertrophy agent such as, for example, sitogluside, a benign prostatic hyperplasia therapy agent such as, for example, tamsulosin hydrochloride, or a prostate growth inhibitor such as, for example, pentomone.

2-nitroimidazole compounds of the invention can also be coupled to a radioactive agent, including, but not limited to: Fibrinogen $^{125}$I; Fludeoxyglucose $^{18}$F; Fluorodopa $^{18}$F; Insulin $^{125}$I; Insulin $^{131}$I; Iobenguane $^{123}$I; Iodipamide Sodium $^{131}$I; Iodoantipyrine $^{131}$I; Iodocholesterol $^{131}$I; Iodohippurate Sodium $^{123}$I; Iodohippurate Sodium $^{125}$I; Iodohippurate Sodium $^{131}$I; Iodopyracet $^{125}$I; Iodopyracet $^{131}$I; Iofetamine Hydrochloride $^{123}$I; Iomethin $^{125}$I; Iomethin $^{131}$I; Iothalamate Sodium $^{125}$I; Iothalamate Sodium $^{131}$I; tyrosine $^{131}$I; Liothyronine $^{125}$I; Liothyronine $^{131}$I; Merisoprol Acetate $^{197}$Hg; Merisoprol Acetate $^{203}$Hg; Merisoprol $^{197}$Hg; Selenomethionine $^{75}$Se; Technetium $^{99m}$Tc Antimony Trisulfide Colloid; Technetium $^{99m}$Tc Bicisate; Technetium $^{99m}$Tc Disofenin; Technetium $^{99}$mTc Etidronate; Technetium $^{99}$mTc Exametazime; Technetium $^{99}$mTc Furifosmin; Technetium $^{99m}$Tc Gluceptate; Technetium $^{99m}$Tc Lidofenin; Technetium $^{99m}$Tc Mebrofenin; Technetium $^{99}$mTc Medronate; Technetium $^{99}$mTc Medronate Disodium; Technetium $^{99}$mTc Mertiatide; Technetium $^{99}$mTc Oxidronate; Technetium $^{99}$mTc Pentetate; Technetium $^{99m}$Tc Pentetate Calcium Trisodium; Technetium $^{99m}$Tc Sestamibi; Technetium $^{99}$mTc Siboroxime; Technetium $^{99}$mTc; Succimer; Technetium $^{99}$mTc Sulfur Colloid; Technetium $^{99m}$Tc Teboroxime; Technetium $^{99m}$Tc Tetrofosmin; Technetium 99mTc Tiatide; Thyroxine $^{125}$I; Thyroxine $^{131}$I; Tolpovidone $^{131}$I; Triolein $^{125}$I; or Triolein $^{131}$I.

2-nitroimidazole compounds of the invention can also include anti-cancer Supplementary Potentiating Agents, including, but not limited to: Tricyclic anti-depressant drugs (e.g., imipramine, desipramine, amitryptyline, clomipramine, trimipramine, doxepin, nortriptyline, protriptyline, amoxapine, and maprotiline); non-tricyclic anti-depressant drugs (e.g., sertraline, trazodone, and citalopram); Ca++ antagonists (e.g., verapamil, nifedipine, nitrendipine, and caroverine); Calmodulin inhibitors (e.g., prenylamine, trifluoroperazine, and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

2-nitroimidazole compounds of the invention that include a therapeutic or cytoxic agent can also be administered with anti-cancer cocktails. Preferred anticancer agents used in anti-cancer cocktails include (some with their MTDs shown in parentheses): gemcitabine (1000 mg/m$^2$); methotrexate (15 gm/m$^2$ i.v.+leuco.<500 mg/m$^2$ i.v. w/o leuco); 5-FU (500 mg/m$^2$/day×5 days); FUDR (100 mg/kg×5 in mice, 0.6 mg/kg/day in human i.a.); FdUMP; Hydroxyurea (35 mg/kg/d in man); Docetaxel (60-100 mg/m$^2$); discodermolide; epothilones; vincristine (1.4 mg/m$^2$); vinblastine (escalating: 3.3-11.1 mg/m$^2$, or rarely to 18.5 mg/m$^2$); vinorelbine (30 mg/m$^2$/wk); meta-pac; irinotecan (50-150 mg/m$^2$, 1×/wk depending on patient response); SN-38 (~100 times more potent than Irinotecan); 10-OH campto; topotecan (1.5 mg/m²/day in humans, 1× iv LDlOmice=75 mg/m²); etoposide (100 mg/m² in man); adriamycin; flavopiridol; Cis-Pt (110 mg/m² in man); carbo-Pt (360 mg/m² in man); bleomycin (20 mg/m2); mitomycin C (20 mg/m²); mithramycin (30 sug/kg); capecitabine (2.5 g/m² orally); cytarabine (100 mg/m²/day); 2-Cl-2'deoxyadenosine; Fludarabine-P04 (25 mg/m²/day, ×5 days); mitoxantrone (12-14 mg/m²); mitozolomide (>400 mg/m²); Pentostatin; or Tomudex.

2-nitroimidazole compounds of the invention can also be prepared by coupling a cytokine (e.g., granulocyte colony stimulating factor) to the compounds. Alternatively, a 2-nitroimidazole of the invention can be administered with one or more immunomodulatory molecules, such as a molecule selected from the group consisting of antibodies, cytokines (e.g., interleukins, interferons, tumor necrosis factor (TNF), granulocyte macrophage colony stimulating factor (GM-CSF), macrophage colony stimulating factor (M-CSF), and granulocyte colony stimulating factor (G-CSF)), chemokines, complement components, complement component receptors, immune system accessory molecules, adhesion molecules, and adhesion molecule receptors.

Therapeutic or cytoxic agents of the invention also include a 2-nitroimidazole of the invention coupled to an antimetabolic agent. Antimetabolites include, but are not limited to, the following compounds and their derivatives: azathioprine, cladribine, cytarabine, dacarbazine, fludarabine phosphate, fluorouracil, gencitabine chlorhydrate, mercaptopurine, methotrexate, mitobronitol, mitotane, proguanil chlorohydrate, pyrimethamine, raltitrexed, trimetrexate glucuronate, urethane, vinblastine sulfate, vincristine sulfate, etc. More preferably, the antimetabolic agent is a folic acid-type antimetabolite, e.g., a class of agents that includes, for example, methotrexate, proguanil chlorhydrate, pyrimethanime, trimethoprime, or trimetrexate glucuronate, or derivatives of these compounds.

In another embodiment, therapeutic or cytoxic agents of the invention include a 2-nitroimidazole of the invention coupled to a member of the anthracycline family of neoplastic agents, including but not limited to aclarubicine chlorhydrate, daunorubicine chlorhydrate, doxorubicine chlorhydrate, epirubicine chlorhydrate, idarubicine chlorhydrate, pirarubicine, or zorubicine chlorhydrate; a camptothecin, or its derivatives or related compounds, such as 10, 11 methylenedioxycamptothecin; or a member of the maytansinoid family of compounds, which includes a variety of structurally related compounds, e.g., ansamitocin P3, maytansine, 2'-N-demethylmaytanbutine, and maytanbicyclinol.

The 2-nitroimidazole compounds of the invention can be coupled directly to a cytotoxic or therapeutic agent using known chemical methods. Alternatively the 2-nitroimidazole compound can be coupled to a cytotoxic or therapeutic agent via an indirect linkage. For example, the 2-nitroimidazole compounds may be attached to a chelating group that is attached to the cytotoxic or therapeutic agent. Chelating groups include, but are not limited to, ininocarboxylic and polyaminopolycarboxylic reactive groups, diethylenetriaminepentaacetic acid (DTPA), and 1,4,7,10-tetraazacyclododecane-1,4,7,10-tetraacetic acid (DOTA). For general methods, see, e.g., Liu et al., Bioconjugate Chem. 12(4):653, 2001; Cheng et al., WO 89/12631; Kieffer et al., WO 93/12112; Albert et al., U.S. Pat. No. 5,753,627; and WO 91/01144 (each of which are hereby incorporated by reference).

When coupled to a therapeutic or cytoxic agent, the specific targeting by the 2-nitroimidazole compounds of the invention allows selective destruction of tumors (e.g., by the action of a boron cluster when irradiated by thermal neutrons, a cytotoxic agent other than a boron cluster, or the combination of a boron cluster and a second cytotoxic agent). 2-nitroimidazole compounds of the invention may be administered to a mammalian subject, such as a human, directly or in combination with any pharmaceutically acceptable carrier, excipient, or salt known in the art, as is discussed in more detail below.

Diagnostic Agents Coupled to Compounds of the Invention

The 2-nitroimidale compounds of the invention can be modified or labeled to facilitate diagnostic or therapeutic uses. Detectable labels, such as a radioactive, fluorescent, heavy metal, or other agent may be bound (ionically or covalently) to the compounds of the invention. Single, dual, or multiple labeling of a compound of the invention may be advantageous. For example, dual labeling with radioactive iodination of one or more residues combined with the additional coupling of, for example, $^{90}Y$ via a chelating group to amine-containing side or reactive groups, would allow combination labeling. This may be useful for specialized diagnostic needs, such as identification of widely dispersed small neoplastic cell masses.

2-nitroimidazole compounds of the invention may also be modified, for example, by halogenation of any one or more of the R1, R2, or R3 groups. Halogens include fluorine, chlorine, bromine, iodine, and astatine. Such halogenated compounds may be detectably labeled, e.g., if the halogen is a radioisotope, such as, for example, $^{18}F$, $^{75}Br$, $^{77}Br$, $^{122}I$, $^{123}I$, $^{124}I$, $^{125}I$, $^{129}I$, $^{131}I$, or $^{211}At$. Other suitable detectable modifications include binding of other compounds (e.g., a fluorochrome, such as fluorescein) to the 2-nitroimidazole compounds of the invention.

Radioisotopes for radiolabeling the 2-nitroimidazole compounds of the invention can be selected from radioisotopes that emit either beta or gamma radiation. Alternatively, the 2-nitroimidazole compounds of the invention can be modified to contain a chelating group. The chelating group can then be modified to contain any of a variety of radioisotopes, such as gallium, indium, technetium, ytterbium, rhenium, or thallium (e.g., $^{125}I$, $^{67}Ga$, $^{111}In$, $^{99}mTc$, $^{169}Yb$, $^{186}Re$).

2-nitroimidazole compounds of the invention that include radioactive metals are useful in radiographic imaging or radiotherapy. Preferred radioisotopes also include $^{99}mTc$, 51Cr, 67Ga, 68Ga, $^{111}In$, $^{168}Yb$, $^{140}La$, $^{90}Y$, $^{88}Y$, $^{153}Sm$, $^{156}Ho$, $^{165}Dy$, $^{64}Cu$, $^{97}Ru$, $^{103}Ru$, $^{816}Re$, $^{188}Re$, $^{203}Pb$, $^{211}Bi$, $^{212}Bi$, $^{213}Bi$, and $^{214}Bi$. The choice of metal is determined based on the desired therapeutic or diagnostic application.

2-nitroimidazole compounds of the invention that include a metal component are useful as diagnostic and/or therapeutic agents. A detectable label may be a metal ion from heavy elements or rare earth ions, such as $Gd^{3+}$, $Fe^{3+}$, $Mn^{3+}$, or $Cr^{2+}$. Conjugates that include paramagnetic or superparamagnetic metals are useful as diagnostic agents in MRI imaging applications. Paramagnetic metals that may be used in conjunction with 2-nitroimidazole compounds of the invention include, but are not limited to, chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), and ytterbium (III). Preferably, the 2-nitroimidazole compounds have a relaxtivity of at least 10, 12, 15, or 20 $mM^{-1}$ $sec^{-1}$ $Z^{-1}$, wherein Z is the concentration of paramagnetic metal.

The 2-nitroimidazole compounds of the invention can be coupled to a chelating agent to form diagnostic agents of the invention. Chelating groups may be used to indirectly couple detectable labels or other molecules to the 2-nitroimidazole compounds of the invention. Chelating groups may be used to link radiolabels to the 2-nitroimidazole compounds of the invention. Examples of chelators known in the art include, for example, the ininocarboxylic and polyaminopolycarboxylic reactive groups, ininocarboxylic and polyaminopolycarboxylic reactive groups, diethylenetriaminepentaacetic acid (DTPA), and 1,4,7,10-tetraazacyclododecane-1,4,7,10-tetraacetic acid (DOTA). Diagnostic agents may be prepared by various methods depending upon the chelator chosen. The 2-nitroimidazole portion of the agent can be prepared by techniques known in the art, and by techniques described in the examples below.

In accordance with one aspect of the invention, 2-nitroimidazole-chelator conjugates incorporate a diagnostically useful metal capable of forming a complex. Suitable metals include, e.g., radionuclides, such as technetium and rhenium in their various forms (e.g., $^{99m}TcO^{3+}$, $^{99m}TcO_{2+}$, $ReO^{3+}$, and $ReO_2^+$). Incorporation of the metal within the conjugate can be achieved by various methods common in the art of coordination chemistry.

When labeled with a diagnostically useful metal, 2-nitroimidazole-chelator conjugates of the present invention can be used to detect hypoxic tissue (e.g., tumor tissue, such as the cancer cells discussed below) by procedures established in the art of diagnostic imaging. A conjugate labeled with a radionuclide metal, such as technetium-99 m, may be administered to a mammal, e.g., a human, by intravenous injection in a pharmaceutically acceptable solution such as isotonic saline, or by other methods described herein. The amount of labeled conjugate appropriate for administration is dependent upon the distribution profile of the chosen conjugate in the sense that a rapidly cleared conjugate may be administered in higher doses than one that clears less rapidly. Unit doses acceptable for imaging hypoxic tissue are in the range of about 5-40 mCi for a 70 kg individual. In vivo distribution and localization can be tracked by standard techniques described herein at an appropriate time subsequent to administration; typically between 30 minutes and 180 minutes depending upon the rate of accumulation at the target site with respect to the rate of clearance at non-target tissue.

Cancers that can be Treated, Prevented, or Detected using the Compounds of the Invention Examples of tumor cells that can be treated, prevented, or detected using the methods and 2-nitroimidazole compounds of the invention include tumor cells of the skin (e.g., squamous cell carcinoma, basal cell carcinoma, or melanoma), breast, colorectal organs, urogenital organs (e.g., prostate, testicles, ovaries, bladder), brain and nervous system, head and neck, pancreas, lung, liver (e.g., hepatoma), kidney, gastrointestinal tract, heart, eyes, stomach, bone, endocrine system (e.g., thyroid and pituitary tumors), and lymphatic system (e.g., Hodgkin's and non-Hodgkin's lymphomas). Cancers of the nervous-system include, for example, astrocytoma, oligodendroglioma, meningioma, neurofibroma, glioblastoma, gliosarcoma, ependymoma, Schwannoma, neurofibrosarcoma, neuroblastoma, and medulloblastoma. Other types of cancers that can be treated using the methods of the invention include fibrosarcoma, neuroectodermal tumor, mesothelioma, epidermoid carcinoma, as well as any other cancers that form solid tumors.

Formulations of the Compounds of the Invention

The 2-nitroimidazole compounds of the invention can be used to preferentially target tumor tissue. Compounds of the invention may be administered to a mammalian subject, such as a human, directly or in combination with any pharmaceutically acceptable carrier or salt known in the art. Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline. Other physiologically acceptable carriers and their formulations are known to one skilled in the art and described, for example, in *Remington's Pharmaceutical Sciences*, (18th edition), ed. A. Gennaro, 1990, Mack Publishing Company, Easton, Pa.

Pharmaceutical formulations of a therapeutically effective amount of a compound of the invention, or pharmaceutically acceptable salt-thereof, can be administered orally, parenterally (e.g., intramuscular, intraperitoneal, intravenous, or subcutaneous injection, inhalation, intradermally, optical drops, or implant), nasally, vaginally, rectally, sublingually, or topically, in admixture with a pharmaceutically acceptable carrier adapted for the route of administration.

Methods well known in the art for making formulations are found, for example, in *Remington's Pharmaceutical Sciences* (18th edition), ed. A. Gennaro, 1990, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the 2-nitroimidazole compounds. Other potentially useful parenteral delivery systems for the 2-nitroimidazole compounds of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

Compositions for rectal or vaginal administration are preferably suppositories which may contain, in addition to active substances, excipients such as coca butter or a suppository wax. Compositions for nasal or sublingual administration are also prepared with standard excipients known in the art. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops or spray, or as a gel.

The amount of active ingredient in the 2-nitroimidazole-containing compositions of the invention can be varied. One skilled in the art will appreciate that the exact individual dosages may be adjusted somewhat depending upon a variety of factors, including the chemical compound being administered, the time of administration, the route of administration, the nature of the formulation, the rate of excretion, the nature of the subject's conditions, and the age, weight, health, and gender of the patient. In addition, the severity of the condition targeted by a 2-nitroimidazole compound of the invention will also have an impact on the dosage level. Generally, dosage levels of between 0.1 µg/kg to 100 mg/kg of body weight are administered daily as a single dose or divided into multiple doses. Preferably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

The 2-nitroimidazole compounds of the invention may be prepared in high yield using simple straightforward methods as exemplified by the examples below. It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

The following examples are provided so that those of ordinary skill in the art can see how to make and use the compounds of the invention. The examples are not intended to limit the scope of what the inventors regard as their invention. All starting materials and reagents are commercially available.

EXAMPLES

We have synthesized a number of boron cluster compounds [III(7), II(10), V(11) and IV(16)]. As shown in Scheme 1, we have prepared conjugated closo-carboranyl [$C_2B_{10}H_{10}$] compounds 3 and 4. Tosylation of 5-Hexyn-1-ol (1) gave 5-hexyn-1-tosylate (2), which was then reacted with acetonitrile-decaborane adduct ($B_{10}H_{12}$-$2CH_3CN$) to produce (3). Subsequent iodination gave closo-1,2-decaboranylethyl-1-(4-Iodo)butane (4).

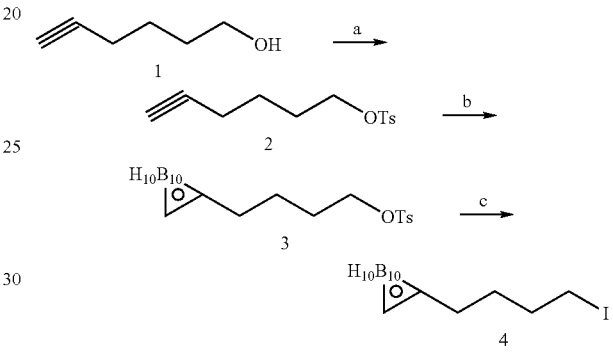

Scheme 1: Synthesis of closo-1,2-decaboranylethyl-1-(4-Iodo)butane

Step a: TsCl/CHCl$_3$/Et$_3$N, room temperature (RT), 12 h, 90%.
Step b: B$_{10}$H$_{14}$/CH$_3$CN, reflux 30 min, then 2 min. in toluene, reflux 20 h, 60%.
Step c: NaI/acetone/RT, 4 h, 97%.

Scheme 2: Synthesis of Boronated 2-Nitroimidazole Compound III

Coupling of 1-(2-nitro-1-imidazolyl)-3-chloro-2-propanol(5) with but-3-ynylamine HCl gave the amine (6). Subsequent alkylation with compound (3) gave the desired boronated compound (7, compound III) in 32% overall yield.

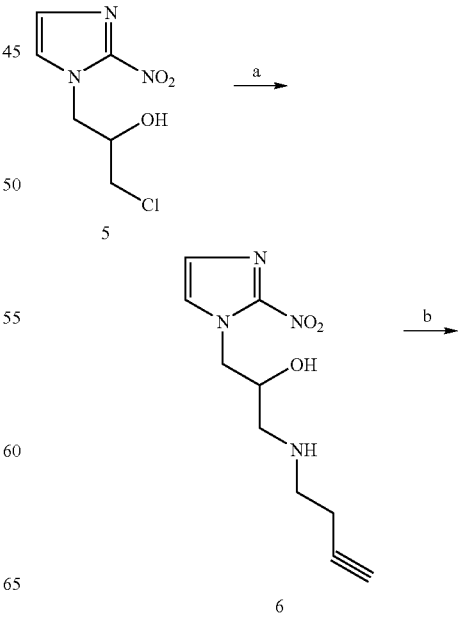

-continued

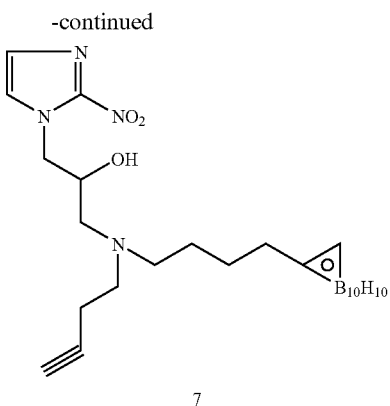
7

Step a: But-3-ynylamine HCl salt/K2CO3/MeOH, reflux, 5 h, 70%.
Step b: 3/NaI/DMF, 85° C., 14 h, 46%.

Scheme 3: Synthesis of Boronated 2-Nitroimidazole Compound II and V.

In order to increase the solubility of boronated compound, a polyether, 2-[-2[(2-Amino-ethoxy)-ethoxy]ethanol chain was employed as the linker and coupled to the 2-nitroimidazole moiety to give the intermediate (15) which was then couple with the carboranyl linker to give the desired compound 16 (III).

-continued

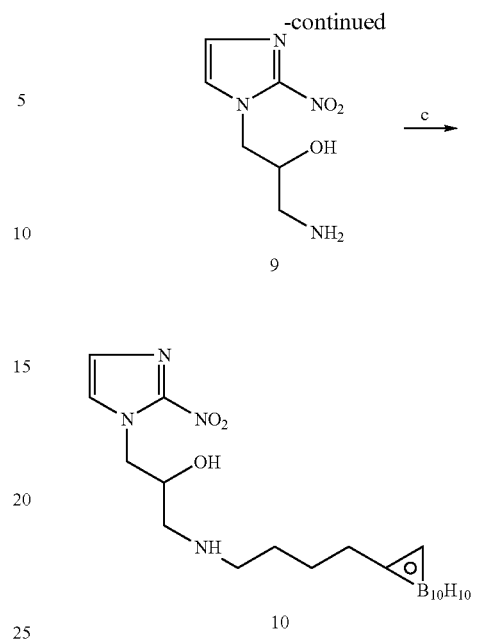

Step a: NaN3/NaI/DMF, 50° C., 2 h, 90%.
Step b: i: Ph3P/THF, 50° C., 2 h, ii: H2O, 50° C., 2 h, 60%.
Step c: 5/EtOH/Et3N, reflux, 5 h, 30%.
Step d: 4/CH3CN, 75° C., 4 h, 40%.
Step e: 2-nitro-1-(oxiranylmethyl)-1H-imidazole (CAS#: 13551-90-1)/CH3CN, 85° C., 12 h, 30%.

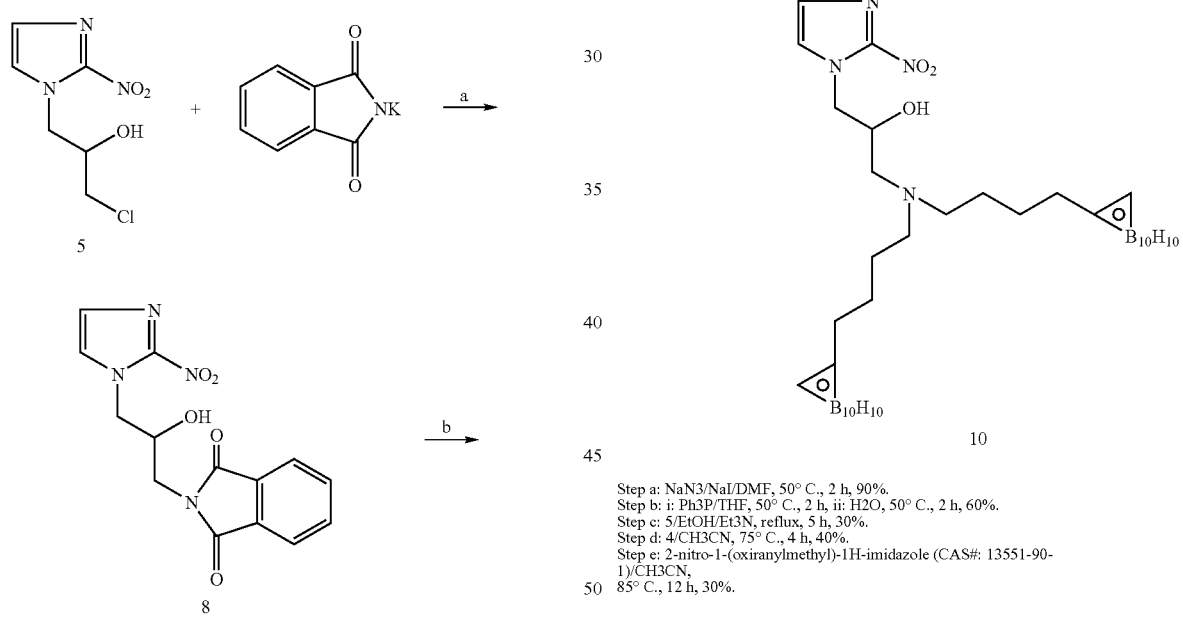

Scheme 4. Synthesis of Boronated 2-Nitroimidazole Compound II and V

Scheme 4 demonstrates a second procedure for synthesizing compounds 10 and 11. The tosylate (3) was converted into its corresponding azide (12) and then followed by reduction with triphenylphosphine to give the intermediate amine (13). Subsequent coupling of the primary amine with 2-nitroimidazole chloride gave the desired carboranyl compound (10, II). Coupling of 2-nitroimidazole epoxide with decarboranyl compound (14) gave the desired compound (11, V).

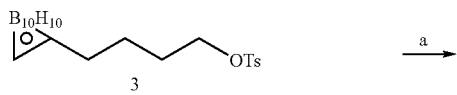

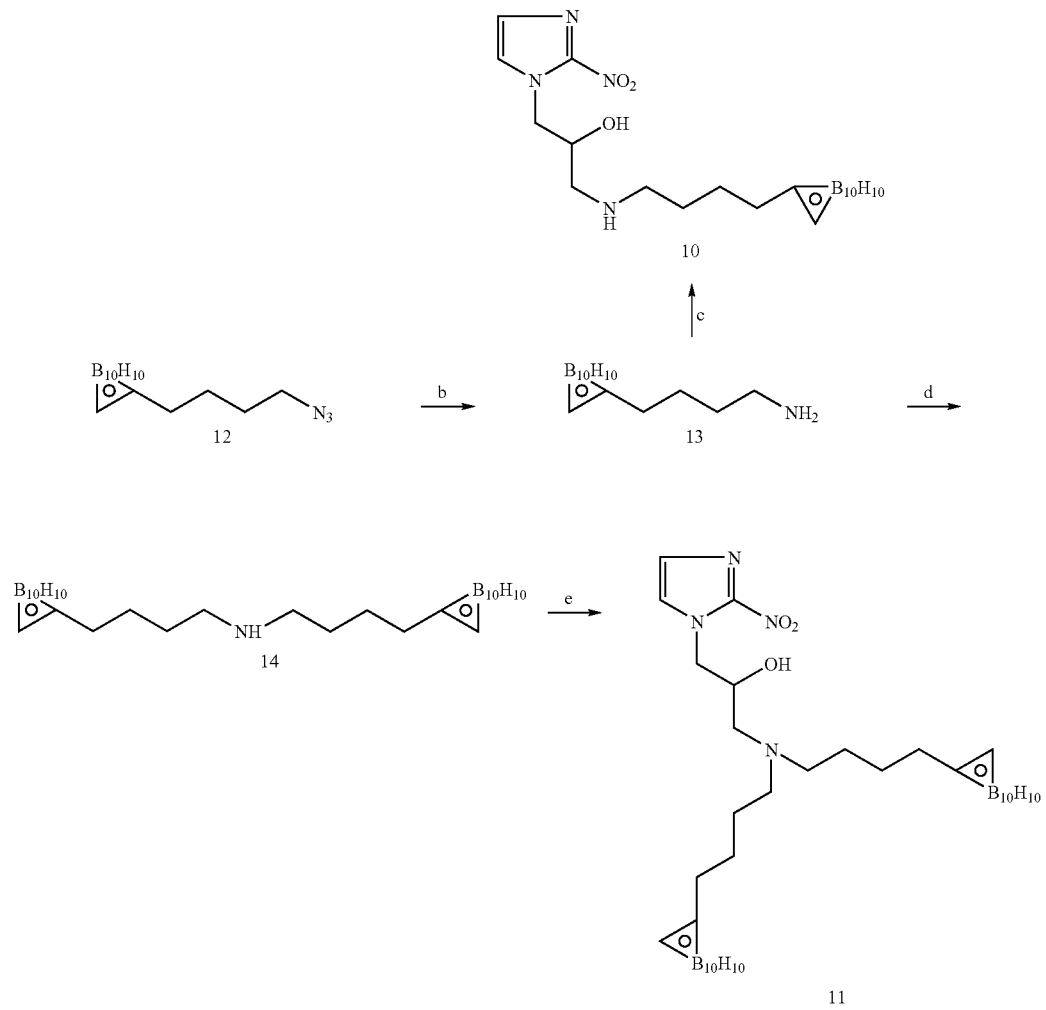
Scheme 5: Synthesis of Boronated 2-Nitroimidazole Compound (16, III).
In order to increase the solubility of boronated compound, a polyether, 2-[2-(2-Amino-ethoxy)-ethoxy]ethanol chain was employed as the linker and coupled to the 2-nitroimidazole moiety to give the intermediate (15) which was then coupled with the carboranyl linker to give the desired compound 16 (III).
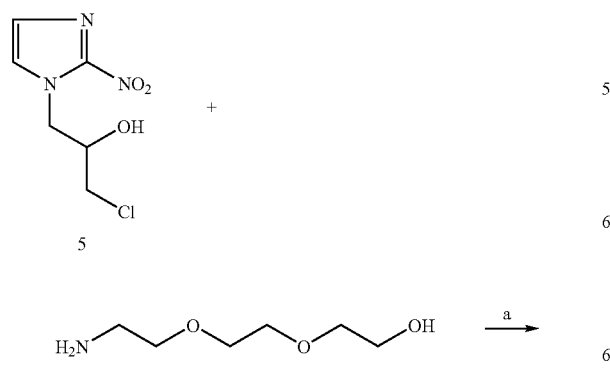
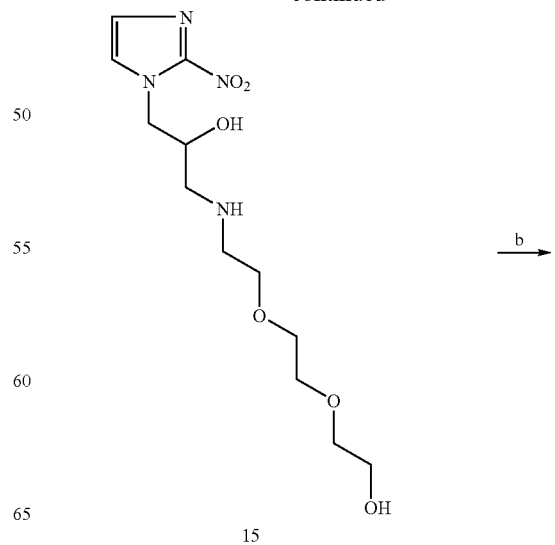

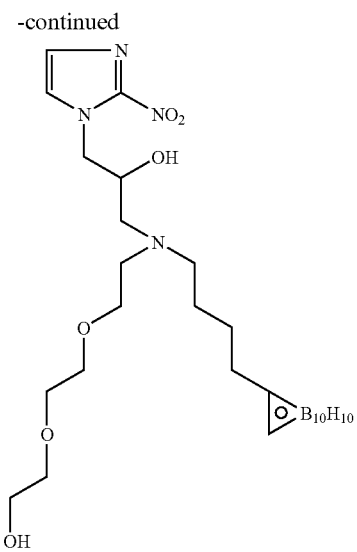

Step a: K₂CO₃/MeOH, 85° C., 14 h, 65%.
Step b: 4/DMF/N₂, 85° C., 2 h, 43%.

Scheme 6 Synthesis of Fluoro-Boronated Compound (18, VI)

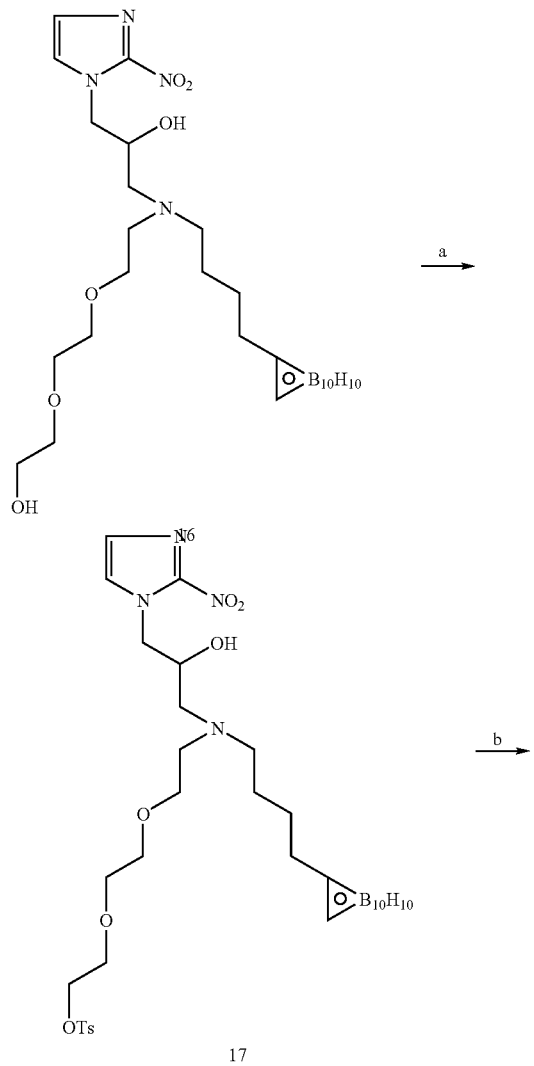

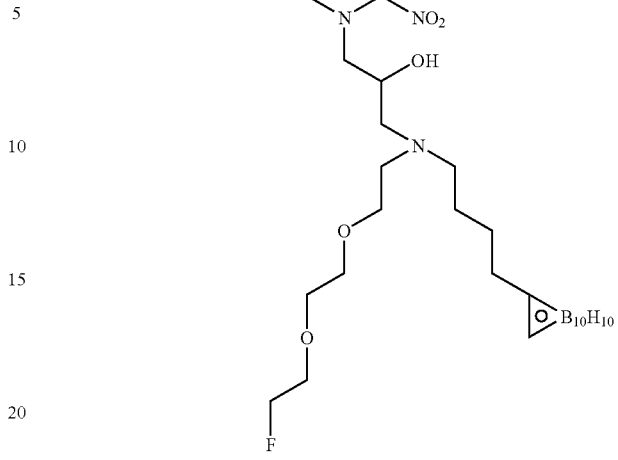

Step a: (TsO)₂O/Et₃N/CH₃COCH₃, 0° C., 2 h, 35%.
Step b: KF/1-Prpanol/N₂, 85° C., 12 h, 47%.

Experimental

General

All chemicals were commercial reagents unless otherwise stated. TLC was performed on silica gel plates (Merck, 60F254). Column chromatography was run on silica gels (60 Å, Merck 230-400 mesh). $^1$H and $^{13}$C NMR spectra were recorded by Varian NMR-300 spectrometers using the deuterated solvents (CDCl₃, DMSO-d₆, CD₃OD and D₂O) and TMS was used as internal standards. Mass spectra were obtained by MALDI-TOF in the positive ion mode.

Synthesis of 5-carboranyl-hexanyl tosylate (2)

Into a mixture of 10 g (0.102 mol) of 5-hexyn-1-ol (1) and 100 ml of CH₃Cl was added 19.5 g (0.102 mol) of p-toluenesulfonyl chloride followed by 18 ml of triethylamine. The reaction mixture was stirred at room temperature for 12 h. TLC (THF: Hexane=1:3) showed that the reaction was completed. Column chromatography (Hexane) gave (2) (23 g, yield 90%) as yellowish oil. $^1$H NMR (CDCl₃, δ$_{ppm}$): 1.54 (m, 2H), 1.75 (m, 2H), 1.90 (t, 1H, —C≡CH, J=2.7 Hz), 2.14 (dt, 2H, —C≡C—CH₂—, J=7.2 Hz, 2.7 Hz), 2.43 (s, 3H, CH₃-Ph), 4.03 (t, 2H, TsO—CH₂, J=6.6 Hz), 7.33 (d, 2H, Ph-, J=8.1 Hz), 7.77 (d, 2H, Ph-, J=8.1 Hz). $^{13}$C NMR (CDCl₃, δ$_{ppm}$): 17.70, 21.62, 24.19, 27.73, 68.94, 69.89, 83.37, 127.86, 129.83, 133.05, 144.74.

Synthesis of 5-hexynyl carborane (3)

Five grams of Decaborane (41 mmol) dissolved in 80 ml of dry acetonitrile and the solution refluxed for 1 h. The solution turned yellow indicating that the acetonitrile-decaborane adduct (B₁₀H₁₂·2CH₃CN) was formed. Then, 11 g (43.7 mmol, 1.07 equivalent) of (2) in 80 ml of dry toluene was added and the reaction mixture refluxed for 20 h. The solvent was evaporated and the residue was purified by column chromatography (EtOAc:Hexane=1:1) to give compound (3, 9.1 g, 60%) as white crystals. $^1$H NMR (CDCl₃, δ$_{ppm}$): 1.46 (m, 2H), 1.61 (m, 2H), 2.14 (t, 2H, [$C_2B_{10}H_{11}$]—$CH_2$—, J=8.7 Hz,), 1.6-3.2 (10H, [$B_{10}H_{10}$]), 3.53 (brs. 1H, carborane-CH), 4.02 (t, 2H, TsO—$CH_2$, J=6.0 Hz), 7.37 (d, 2H, Ph-, J=8.4 Hz), 7.78 (d, 2H, Ph-, J=8.4 Hz). $^{13}C$ NMR (CDCl$_3$, $\delta_{ppm}$): 21.64, 25.27, 28.01, 37.22, 61.08 (carborane-CH), 69.38, 74.57 (carborane-C), 127.81, 129.97, 132.78, 145.10.

Synthesis of closo-1,2-decaboranylethyl-1-(4-Iodo)butane (4)

Five grams (13.5 mmol) of (3) and 7.3 g (48 mmol) of sodium iodide were dissolved in 100 ml of acetone and the resulting mixture stirred at room temperature for 6 h. After workup, the solvent was evaporated and the residue purified by column chromatography (EtOAc:Hexane=1:1) to give compound (4, 4.2 g, 80%) as a white solid. $^1H$ NMR (CDCl$_3$, $\delta_{ppm}$): 1.60 (m, 2H), 1.78 (m, 2H), 2.22 (t, 2H, [$C_2B_{10}H_{11}$]—$CH_2$—, J=8.4 Hz,), 1.6-3.2 (10H, [$B_{10}H_{10}$]), 3.16 (t, 2H, I—$CH_2$, J=6.0 Hz), 3.60 (brs. 1H carborane-CH). $^{13}C$ NMR (CDCl$_3$, $\delta_{ppm}$): 5.42, 30.41, 32.55, 37.24 61.45 (carborane-CH), 75.09 (carborane-C).

Synthesis of 1-(2-nitro-1-imidazolyl)-3-chloro-2-propanol (5)

Epichlorohydrin (100 mL) was added to a mixture of 2-nitroimidazole (11.3 g, 0.1 mol) and 1 g of potassium carbonate and the solution refluxed for 15-20 min until all 2-nitroimidazole was dissolved. The hot solution was filtered and the yellow crystal was collected to give compound (5, 17 g, 83%). $^1H$ NMR (DMSO-d$_6$, $\delta_{ppm}$): 3.61 (m, 2H, Cl—$CH_2$—), 4.06 (m, 1H, HO—CH—), 4.32 (dd, 1H, N—$CH_a$—, J=13.8 Hz, 8.4 Hz), 4.63 (dd, 1H, N—$CH_b$—, J=13.8 Hz, 3.6 Hz), 5.67 (d, 1H, OH, J=5.7 Hz), 7.15 (s, 1H, —CH=), 7.56 (s, 1H, —CH=). $^{13}C$ NMR (DMSO-d$_6$, $\delta_{ppm}$): 46.81, 52.27, 68.75, 127.40, 128.45, 144.98.

Synthesis of 1-but-3-ynylamino-3-(2-nitro-imidazol-1-yl)-propan-2-ol (6)

A mixture of 5 (2.67 g, 13.1 mmol), but-3-ynylamine HCl salt (2.76 g, 26.2 mmol) and potassium carbonate (3.62 g) in 40 ml of methanol was refluxed for 5 h. After the workup, the residue was purified by column chromatography (THF-EtOH=9:0.5) to give 2.2 g of yellow solid (6, 70% yield). $^1H$ NMR (DMSO-d$_6$, $\delta_{ppm}$): 2.26 (dt, 2H, ≡C—$CH_2$—, J=7.2 Hz, 2.7 Hz), 2.50 (d, 2H, J=5.7 Hz), 2.63 (t, 2H, J=7.2 Hz), 2.78 (t, 1H, CH≡C—, J=2.7 Hz), 3.82 (m, 1H, HO—CH—), 4.25 (dd, 1H, imidazole-$CH_a$—, J=13.8 Hz, 8.4 Hz), 4.54 (dd, 1H, imidazole-$CH_b$—, J=13.8 Hz, 3.6 Hz), 5.13 (d, 1H, OH, J=5.1 Hz), 7.13 (s, 1H, —CH=), 7.55 (s, 1H, —CH=). $^{13}C$ NMR (DMSO-d$_6$, $\delta_{ppm}$): 18.80, 47.79, 52.04, 52.89, 68.09, 71.60, 82.87, 126.98, 128.19, 144.83.

Synthesis of 1-[but-3-ynyl-(4-(1,2-closo-decaboranylethyl)-butyl)-amino]-3-(2-nitro-imidazol-1-yl)-propan-2-ol (7)

To a mixture of (6) (238 mg, 1 mmol), (3) (370 mg, 1 mmol) and sodium iodide (300 mg, 2 mmol) was added 20 ml of DMF and the resulting solution was stirred at 85° C. for 14 h. After workup, the residue was purified by column chromatography (EtOAc:Hexane=1:1) to give 200 mg of yellowish solid (7, 46% yield). $^1H$ NMR (CDCl$_3$, $\delta_{ppm}$): 1.38-1.55 (m, 4H), 2.21 (m, 2H), 2.31 (m, 2H), 2.46-2.73 (m, 7H), 1.2-3.1 (10H, [$B_{10}H_{10}$]), 3.58 (brs. 1H, carborane-CH), 3.96 (m, 1H, HO—CH—), 4.24 (dd, 1H, imidazole-$CH_a$—, J=13.8 Hz, 7.5 Hz), 4.68 (d, 1H, imidazole-$CH_b$—, J=13.8 Hz), 7.16 (s, 1H, —CH=), 7.30 (s, 1H. —CH=). $^{13}C$ NMR (CDCl$_3$, $\delta_{ppm}$): 17.72, 26.67, 26.70, 37.87, 52.32. 53.04, 53.48, 57.06, 61.08 (carborane-CH), 66.77, 69.94, 74.92 (carborane-C), 82.39, 127.53, 128.14. TOF MS (m/e): 436.5 (M$^+$. 68%), 437.5 (M+1, 90%), 438.5 (M+2, 100%).

Synthesis of 2-[2-hydroxy-3-(2-nitro-imidazol-1-yl)-propyl]-isoindole-1,3-dione (8)

A mixture of (5, 4.74 g, 23 mmol) and phthalimide potassium salt (4.27 g, 23 mmol) was dissolved in 50 ml of DMF and the resulting solution was stirred at 85° C. for 2 h. The reaction mixture was poured into 60 ml of CH$_2$Cl$_2$ and 150 ml of water. The white solid was filtered, washed by water and dichloromethane and dried to give 6.3 g of (8, 87% yield). $^1H$ NMR (DMSO-d$_6$, $\delta_{ppm}$): 3.60 (m, 2H), 4.06 (m, 1H, HO—CH—), 4.25 (dd, 1H, imidazole-$CH_a$—, J=13.8 Hz, 8.7 Hz), 4.57 (dd, 1H, imidazole-$CH_b$—, J=13.8 Hz, 3.0 Hz), 5.13 (d, 1H, OH, J=5.7 Hz), 7.12 (d, 1H, J=0.9 Hz, —CH=), 7.59 (d, 1H, J=0.9 Hz, —CH=), 7.84 (m, 4H, phenyl proton). $^{13}C$ NMR (DMSO-d$_6$, $\delta_{ppm}$): 41.42, 52.65, 66.90, 123.04, 127.34, 128.42, 131.67, 134.38, 144.94, 167.91.

Synthesis of 1-amino-3-(2-nitro-imidazol-1-yl)-propan-2-ol (9)

Compound 8 (5 g, 15.8 mmol) was added to a solution of pure hydrazine (608 mg, 18.97 mmol, 1.2 equivalent) in 50 ml of ethyl alcohol and 4 ml of water. The mixture was refluxed for 2 h and then held at room temperature. The white solid (phthalhydrazide) was filtered. The filtrate was concentrated and the residue was redistributed in ethyl acetate and water. The water phase was extracted two times with ethyl acetate and the combined ethyl acetate phase was dried to give a yellowish solid as the HCl salt (9, 2.45 g, 70% yield). $^1H$ NMR (D$_2$O, $\delta_{ppm}$)(HCl salt): 2.91 (dd, 1H, NH$_2$—$CH_a$, J=13.2 Hz, 9.9 Hz), 3.21 (dd, 1H, NH$_2$—$CH_b$, J=13.2 Hz, 2.7 Hz), 4.19 (tt, 1H, HO—CH—, J=9.0 Hz, 3.0 Hz), 4.28 (dd, 1H, imidazole-$CH_a$—, J=13.8 Hz, 8.7 Hz), 4.57 (dd, 1H, imidazole-$CH_b$—, J=13.8 Hz, 2.7 Hz), 7.09 (d, 1H, J=0.9 Hz, —CH=), 7.35 (d, 1H, J=0.9 Hz, —CH=). $^{13}C$ NMR (D$_2$O, $\delta_{ppm}$): 42.06, 53.00, 66.86, 128.06, 128.92, 144.73.

Synthesis of 1-[4-(closo-1,2-decaboranylethyl)-butyl)-amino]-3-(2-nitro-imidazol-1-yl)-propan-2-ol (10)

A mixture of (9, 330 mg, 1.78 mmol) and 4 (695 mg, 2.13 mmol, 1.2 equivalent) was dissolved in 15 ml of acetonitrile and the resulting solution was refluxed for 18 h. After workup, the residue was purified by column chromatography (EtOH:EtOAc=1:6 to 1:2) to give 182 mg of white solid as iodide salt (10, 20% yield). $^1H$ NMR (CD$_3$OD, $\delta_{ppm}$): (HI salt): 1.54-1.72 (m, 4H), 2.33 (m, 2H), 3.02 (m, 3H), 1.2-3.1 (10H, [$B_{10}H_{10}$]), 3.22 (dd, 1H, J=12.6 Hz, 2.4 Hz), 4.29 (m, 1H, HO—CH—), 4.40 (dd, 1H, imidazole-$CH_a$—, J=13.8 Hz, 7.8 Hz), 4.56 (brs. 1H, carborane-CH), 4.68 (dd, 1H, imidazole-$CH_b$—, J=13.8 Hz, 3. 0Hz), 7.16 (d, 1H, J=1.2 Hz, —CH=), 7.49 (d, 1H, J=1.2 Hz, —CH=). $^{13}C$ NMR (CD$_3$OD, $\delta_{ppm}$): 26.39, 27.45, 38.13, 48.53, 51.07, 54.12, 63.79 (carborane-CH), 66.83, 76.68 (carborane-C), 128.50, 129.34. TOF MS (m/e): 384.3 (M$^+$, 65%), 385.3 (M+1, 100%), 386.3 (M+2, 95%).

From compound 13: 206 mg (1 mmol) of 5 and 215 mg (1 mmol) of 13 were dissolved in a solution of 15 ml of ethyl alcohol and 1 ml of triethylamine and the solution refluxed for 5 h. 200 mg of product was obtained as the free base by column chromatography (EtOH:EtOAc=1:6), yield is 52%.

Synthesis of 1-[di-(4-(closo-1,2-decaboranyl ethyl)-butyl))-amino]-3-(2-nitro-imidazol-1-yl)-propan-2-ol (11)

A mixture of compound 10 (200 mg) and (4) (204 mg) was dissolved in 10 ml of acetonitrile and 1 ml of triethylamine. The reaction mixture was stirred at 85° C. for 8 h. After workup, the residue was purified by column chromatography (EtOAc:Hexane=5:1 to EtOAc) to give 31 mg of product (11, 10% yield) (CD$_3$OD, $\delta_{ppm}$): 1.43-1.52 (m, 8H), 2.30 (m, 4H), 2.49 (m, 8H), 1.4-3.2 (20H, 2×[B$_{10}$H$_{10}$]), 3.99 (m, 1H, HO—CH—), 4.17 (dd, 1H, imidazole-CH$_a$—, J=13.5 Hz, 9.0 Hz), 4.49 (brs. 2H, carborane-CH), 4.79 (dd, 1H, imidazole-CH$_b$—, J=13.5 Hz, 2.7 Hz), 7.13 (d, 1H, J=1.2 Hz, —CH═), 7.45 (d, 1H, J=1.2Hz, —CH═). $^{13}$CNMR (CD$_3$OD, $\delta_{ppm}$): 27.52, 28.33, 38.75, 55.26, 55.45, 59.39, 63.56 (carborane-CH), 69.13, 77.27 (carborane-C), 128.13, 129.44. TOF MS (m/e): 582.8 (M$^+$, 75%), 583.8 (M+1, 100%), 584.8 (M+2, 95%).

From compound 14: A mixture of (14) (0.6 g, 1.45 mmol) and 0.3 g (1.78 mmol, 1.2 equivalent) of 2-nitro-1-(oxiranyl-methyl)1H-imidazole in 15 ml of CH$_3$CN was reacted at 85° C. for 12 h. After workup, the residue was purified by column chromatography (EtOAc:Hexane=5:1 to EtOAc) to give 254 mg of pure product (11, 30% yield).

Synthesis of 1,2-Dicarba-closo-dodecaboran (12) ylethyl-1(4-azido)butane (12)

Sodium azide (NaN$_3$; 1.58 g; 24.3 mmol, 1.5 equivalent) was added to the solution of 6 g (16.2 mmol) of 3 in 30 ml of DMF. The reaction mixture was stirred at 50° C. for 2 h and DMF then removed under vacuum. The residue was distributed in 10 ml of ethyl acetate and 5 ml of water. The organic phase was separated, concentrated and purified by column chromatography (EtOAc:Hexane=1:4) to give 3.52 g of white solid (12, 90% yield) $^1$H NMR (CDCl$_3$, $\delta_{ppm}$) 1.57 (m, 4H), 2.23 (m, 2H), 2.31 (m, 2H), 1.2-3.1 (10H, [B$_{10}$H$_{10}$]), 3.57 (brs. 1H, carborane-CH). $^{13}$CNMR (CDCl$_3$, $\delta_{ppm}$): 26.45, 28.21, 37.61, 50.79, 61.05 (carborane-CH), 74.72 (carborane-C).

Synthesis of closo-1,2-caboranylethyl-1-(4-amino)butane (13)

A mixture of 3.5 g (14.5 mmol) of 12 and 4.2 g of triphenylphosphine (16 mmol, 1.1 equivalent) was dissolved in 40 ml of THF and the resulting solution was stirred at 50° C. for 2 h. 10 ml of water was added and stirring continued at 50° C. for 2 h. 1.87 g (60% yield) colorless oil was obtained after column chromatography (EtOAc to EtOAc:EtOH=6:1). $^1$H NMR (CD$_3$OD, $\delta_{ppm}$)(HCl salt): 1.62 (m, 0.4H), 2.33 (m, 2H), 2.93 (t, 2H, J=7.2 Hz), 1.2-3.0 (10H, [B$_{10}$H$_{10}$]), 4.57 (brs. 1H, carborane-CH). $^{13}$C NMR (CD$_3$OD, $\delta_{ppm}$): 27.39, 27.97, 38.17, 40.28, 63.84 (carborane-CH), 76.73 (carborane-C).

Synthesis of bis-[4-(closo-1,2-decaboranylethyl)-butyl]-amine (14)

HCl salt (300 mg; 1.2 mmol) of 13 and 326 mg (1.0 mmol) of (4) were added to a solution of 10 ml of CH3CN and 0.5 ml of Et3N. The reaction mixture was stirred at 75□ for 4 h. After workup, the residue was purified by column chromatography (EtOAc:EtOH=12: 1) to give 200 mg of (14, 40% yield) as a yellowish solid. 1H NMR (CD3OD, δppm): 1.62 (m, 8H), 2.35 (m, 4H), 2.99 (t, 4H, J=6.6 Hz), 1.2-3.1 (20H, 2×[B10H10]), 4.57 (brs. 2H, 2× carborane-CH). 13CNMR (CD3OD, δppm): 26.82, 27.52, 38.13, 48.53, 63.82 (carborane-CH), 76.75 (carborane-C).

Synthesis of Compound (15)

A mixture of 1.03 g (5 mmol) of 5 and 1.49 g (10 mmol) of 2-[2-(2-amino-ethoxy)-ethoxy]-ethanol was dissolved in methanol and then 0.7 g (5 mmol) of potassium carbonate was added. The reaction mixture was refluxed for 14 h. After workup the residue was purified by column chromatography (EtOH to EtOH:H2O=2:1) to give, 800 mg of an oily product (15, 65% yield) along with 200 mg of recovered starting material. $^1$H NMR (DMSO-d$_6$, $\delta_{ppm}$): 2.70-2.95 (m, 4H, —CH$_2$—NH—CH$_2$—), 3.55-3.73 (m, 10H, 5×-OCH$_2$), 4.13 (m, 1H, OCH), 4.42 (dd, 1H, imidazole-CH$_a$—, J=13.8 Hz, 8.7 Hz), 4.68 (dd, 1H, imidazole-CH$_b$—, J=13.8 Hz, 3.3 Hz), 7.18 (s, 1H, —CH═), 7.57 (s, 1H, —CH═). $^{13}$C NMR (DMSO-d$_6$, $\delta_{ppm}$): 49.57, 53.03, 54.44, 61.93, 68.41, 69.04, 69.93, 71.21, 73.67, 128.45, 129.57, 146.45.

Synthesis of Compound (16)

A mixture of 2.3 g (7.2 mmol) of compound (15) and 2.83 g (8.7 mmol, 1.2 equivalent) of compound (4) was dissolved in 20 ml of DMF. The reaction mixture was stirred at 85° C. for 2 h under nitrogen. DMF was removed under vacuum. The residue was redistributed in EtOAc—H$_2$O (20 ml-20 ml). The organic phase was separated and water phase was extracted with acetyl acetate (20 ml) twice. The combined EtOAc was concentrated and the residue was purified by column chromatography (EtOAc:EtOH=2:1 to 1:1) to give 1.6 g of yellowish (16, 43% yield). $^1$H NMR (CD$_3$OD, $\delta_{ppm}$): 1.41-1.54 (m, 4H), 2.29 (m, 2H), 2.56 (m, 4H, N—(CH$_2$)$_2$), 2.70 (t, 2H, N—CH$_2$, J=5.7 Hz), 1.4-3.1 (10H, [B$_{10}$H$_{10}$]), 3.51-3.64 (m, 10H, 5×-OCH$_2$), 3.99 (m, 1H, HO—CH—), 4.24 (dd, 1H, imidazole-CH$_a$—, J=13.8 Hz, 8.7 Hz), 4.51 (brs. 1H, carborane-CH), 4.79 (dd, 1H, imidazole-CH$_b$—, J=13.8 Hz, 2.7 Hz), 7.13 (s, 1H, —CH═), 7.47 (s, 1H, —CH═). $^{13}$CNMR (CD$_3$OD, $\delta_{ppm}$): 27.66, 28.18, 38.73, 54.98, 55.20, 56.16, 59.69, 62.20, 63.61 (carborane-CH), 69.46, 70.79, 71.42, 73.67, 77.36 (carborane-C), 128.06, 128.30. TOF MS (m/e): 516.5 (M$^+$, 85%), 517.5 (M+1, 100%), 518.5 (M+2, 95%).

Synthesis of 1-{2-[2-(2-Tosyl-ethoxy)-ethoxy]-ethyl-(4-(1,2-Dicarba-closo-dodecaboran(12)ylethyl)-butyl)-amino}]-3-(2-nitro-imidazol-1-yl)-propan-2-ol (17)

Compound 16 (188 mg; 0.36 mmol) and 126 mg (0.38 mmol) of p-toluenesulfonic anhydride were dissolved in 20 ml of dried acetone and 1 ml of triethylamine. Stirred at 0° for 2 h then remove acetone by rotary evaporator. The residue was dissolved in 0.5 ml of EtOH and direct purified by column chromatography (EtOAc:EtOH=10:1), 80 mg yellowish oil was obtained with 31% yield. 1H NMR (CD3OD, δppm): 1.43-1.55 (m, 4H), 2.29 (m, 2H), 2.44 (s, 3H, CH3), 2.56 (m, 4, N—(CH2)2), 2.67 (t, 2H, N—CH2, J=5.7 Hz), 1.4-3.2 (10H, [B10H10]), 3.54 (brs., 6H, 3×-OCH2), 3.63 (t, 2H, —OCH2, J=2.4 Hz), 3.96 (m, 1H, HO—CH—), 4.09 (t, 2H, —CH2OTs, J=2.4 Hz), 4.24 (dd, 1H, imidazole-CH$_a$—, J=13.8 Hz, 9.0 Hz), 4.47 (brs, 1H, carborane-CH), 4.79 (dd, 1H, imidazole-CH$_b$—, J=13.8 Hz, 2.4 Hz), 7.10 (d, 1H, —CH═, J=1.2 Hz), 7.41 (d, 1H, —CH═, J=1.2 Hz), 7.45 (d, 2H, benzene, J=8.1 Hz), 7.76 (d, 2H, benzene, J=8.1 Hz). 13CNMR (CD3OD, δppm): 21.63, 27.60, 28.16, 38.68, 54.98, 55.13, 56.02, 59.59, 63.54

(carborane-CH), 69.35, 69.71, 70.73, 70.92, 71.26, 71.58, 77.36

(carborane-C), 128.05, 129.03, 129.33, 131.08, 134.36, 146.50.

Synthesis of 1-{2-[2-(2-Fluoro-ethoxy)-ethoxyl-ethyl-(4-(1,2-Dicarba-closo-dodecaboran(12)yl-ethyl)-butyl)-amino}]-3-(2-nitro-imidazol-1-yl)-propan-2-ol (18)

Compound 17 (188 mg; 0.36 mmol) and 31 mg (0.08 mmol) of Kryptofix 222 were dissolved in 5 ml of acetonitrile (CH3CN). To this solution was added anhydrous potassium fluoride (99.99+%, 12 mg, 0.2 mmol). After the tosylate was totally dissolved, the reaction mixture was reflux for 2 h in an oil bath at 85° C. After workup, the crude reaction product was purified by column chromatography (EtOAc-EtOH=5:1 to 3:1) to afford 10 mg of target fluorinated product 18 with 47% yield. 1H NMR (CD3OD, δppm): 1.42-1.56 (m, 4H), 1.60-1.72 (m, 2H), 2.83 (m, 4H, N—(CH2)2), 3.06 (m, 2H, N—CH2), 1.4-3.2 (10H, [B10H10]), 3.65 (m, 10H, 4x-OCH2, F—CH2), 4.20 (m, 1H, HO—CH—), 4.42 (m, 1H, imidazole-CHa-,), 4.61 (m, 1H, carborane-CH), 4.79 (m, 1H, imidazole-CHb-), 7.10 (s, 1H, —CH═), 7.42 (s, 1H, —CH═). 13CNMR (CD3OD, δppm): 30.05, 30.75, 40.55, 54.87, 55.18, 56.80, 59.28, 61.54 (carborane-CH), 71.05, 71.36, 71.43, 71.50, 71.63, 71.69, 74.02 (carborane-C), 84.11 (d, JF-C=166.6 Hz), 128.07, 129.26, 145.51.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

What is claimed is:

1. A compound having the structure of formula I and pharmaceutically acceptable salts thereof

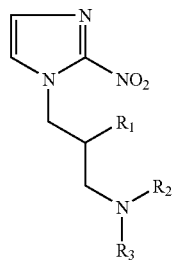

wherein:
R1 is a halogen, positron emitting radionuclide, non-metal, lower alkyl substituted to contain a halogen, lower alkyl substituted to contain a positron emitting radionuclide, lower alkyl substituted to contain a non-metal, tosylate, mesylate, tryflate, hydrogen, or hydroxyl; and R2 and R3 are independently selected from a lower alkyl, allyl, alkenyl, alkynyl, hydroxyalkyl, heteroalkyl, polyether, and polyether with a terminal heteroatom and wherein at least one of R2 or R3 comprises a boron cluster and, optionally, a therapeutic agent, cytotoxic agent, detectable label, or chelating group.

2. The compound of claim 1, wherein said therapeutic agent is an antibiotic, a supplementary potentiating agent, an hormonal agonist or antagonist, an apoptotic agent, or an immunomodulator.

3. The compound of claim 1, wherein said cytotoxic agent is a radiosensitizer, an alkylating agent, an antineoplastic agent, an antiproliferative agent, an antimetabolic agent, a tubulin inhibitor, or a topoisomerase I or II inhibitor.

4. The compound of claim 1, wherein said boron cluster is decaborane, dodecaborane, closo-1,2-carborane, or methyl-o-carborane.

5. The compound of claim 3, wherein said cytotoxic agent is camptothecin, homocamptothecin, colchicine, combretastatin, dolastatin, doxorubicin, methotrexate, podophyllotoxin, rhizoxin, rhizoxin D, a taxol, paclitaxol, cisplatin, CC1065, or a maytansinoid.

6. The compound of claim 1, wherein R1 is a halogen or a non-metal.

7. The compound of claim 6, wherein said halogen is $^{18}$F or $^{19}$F.

8. The compound of claim 1, wherein R2 and R3 comprise a therapeutic or a cytotoxic agent.

9. The compound of claim 8, wherein said therapeutic or cytotoxic agent is the same or different.

10. The compound of claim 1, wherein said detectable label is a radiolabel selected from $^{11}$C, $^{13}$N, $^{15}$O, $^{18}$F, $^{52}$Fe, $^{55}$CO, $^{61}$Cu, $^{62}$Cu, $^{64}$Cu, $^{67}$Cu, $^{67}$Ga, $^{68}$Ga, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{111}$In, $^{120}$I, $^{123}$I, $^{124}$I, $^{125}$I, $^{131}$I, $^{122}$Xe, $^{175}$Lu, $^{154}$Gd, $^{71}$As, $^{74}$As, $^{76}$Br, X$^{175}$Lu, $^{154}$Gd, $^{155}$Gd, $^{156}$Gd, $^{157}$Gd, $^{158}$Gd, $^{94m}$Tc, $^{94}$Tc, and $^{99m}$Tc.

11. The compound of claim 1, wherein R2 or R3 is a polyether that terminates with a boron cluster.

12. The compound of claim 1, wherein said therapeutic agent, cytotoxic agent, detectable label, or chelating group is attached to said compound by an enzymatically cleavable bond.

13. The compound of claim 1, wherein said chelating agent is an ininocarboxylic reactive group, a polyaminopolycarboxylic reactive group, diethylenetriaminepentaacetic acid (DTPA), or 1,4,7,10-tetraazacyclododecane-1,4,7,10-tetraacetic acid (DOTA).

14. The compound of claim 1, wherein said heteroatom is selected from nitrogen, oxygen, and sulfur atoms.

15. The compound of claim 14, wherein said therapeutic agent is covalently bonded to said compound through said heteroatom.

16. The compound of claim 1, wherein said compound has the structure of any one of the following:

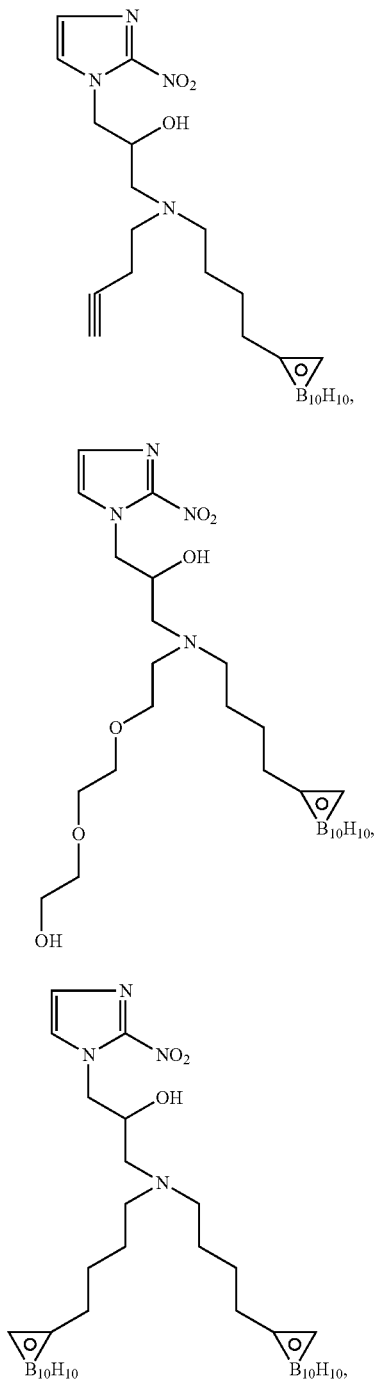

17. The compound of claim 1, admixed with a pharmaceutically acceptable carrier or excipient.

18. The compound of claim 1, wherein said compound is in salt form with an anionic counterion.

19. The compound of claim 18, wherein said counterion is a halide.

20. A method of treating a hypoxic condition in a patient in need thereof comprising administering the compound of claim 1 to said patient.

21. The method of claim 20, wherein R2 or R3 of said compound contains a boron cluster.

22. The method of claim 21, wherein said boron cluster is decaborane, dodecaborane, closo-1,2-carborane, or methyl-o-carborane.

23. The method of claim 20, wherein said compound further comprises a cytotoxic agent.

24. The method of claim 21, wherein said method comprises boron neutron capture therapy (BNCT).

25. The method of claim 20, wherein said compound is administered with a pharmaceutically acceptable carrier or excipient.

26. The method of claim 20, wherein said hypoxic condition is associated with a solid tumor, inflammation, or ischemia.

27. The method of claim 26, wherein said solid tumor is a glioblastoma, gliosarcoma, or melanoma.

28. The method of claim 20, wherein said compound has the structure of any one of the following:

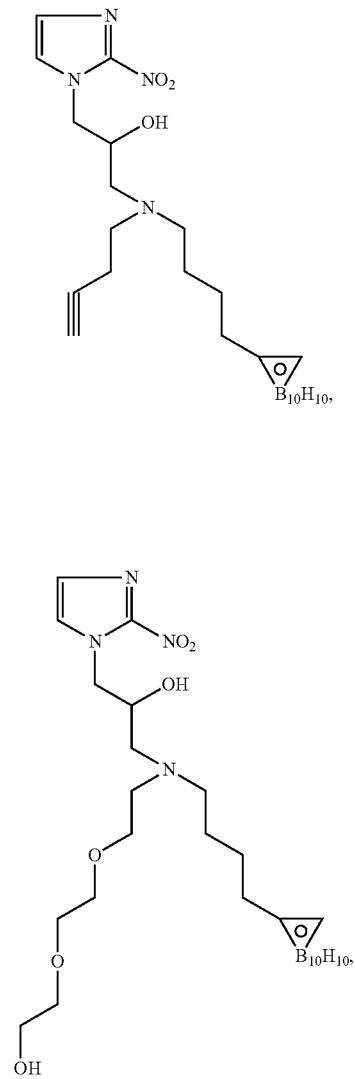

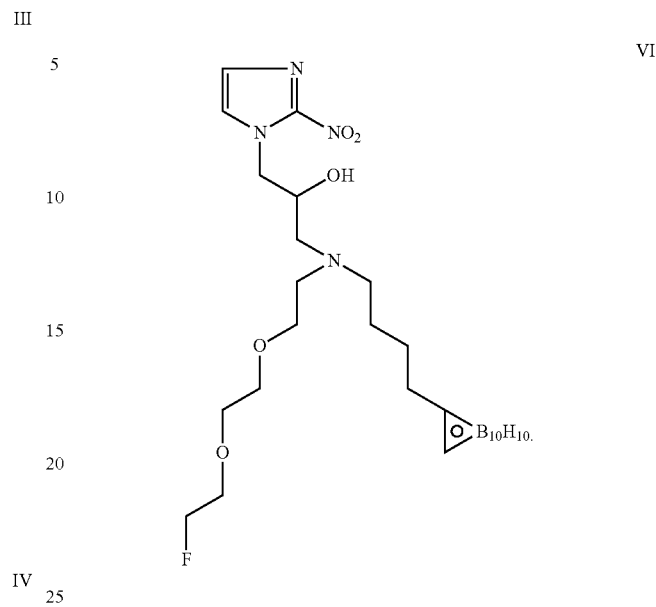

29. A method for detecting hypoxic cells in a mammal comprising administering to said mammal the compound of claim 1, wherein said compound comprises a radionuclide at R1, and detecting any of said compound retained in tissue of said mammal by non-invasive positron emission tomography (PET); or wherein said compound comprises a halogen or a non-metal at R1, and detecting any of said compound retained in said tissue by magnetic resonance spectroscopy (MRI) or magnetic resonance imaging (MRI).

30. The method of claim 29, wherein said radionuclide is $^{18}$F.

31. The method of claim 29, wherein R2 or R3 of said compound comprises a therapeutic agent, cytotoxic agent, detectable label, or chelating group.

32. The method of claim 29, wherein said compound has the structure of any one of the following:

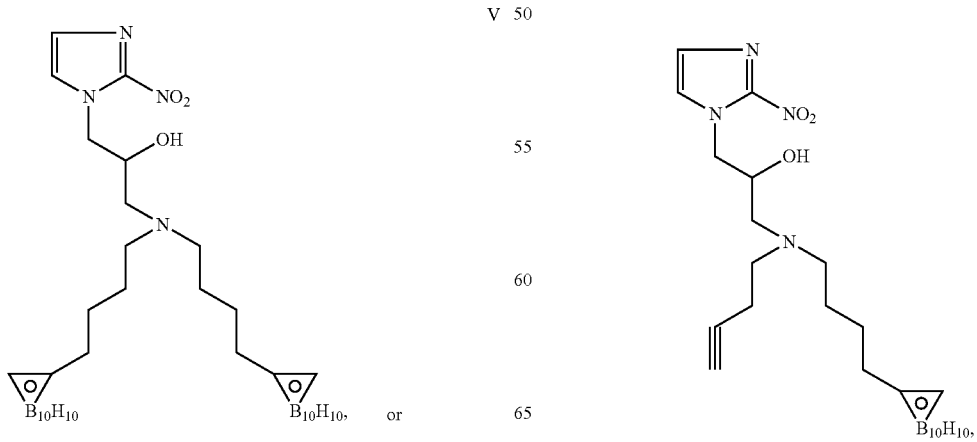

IV

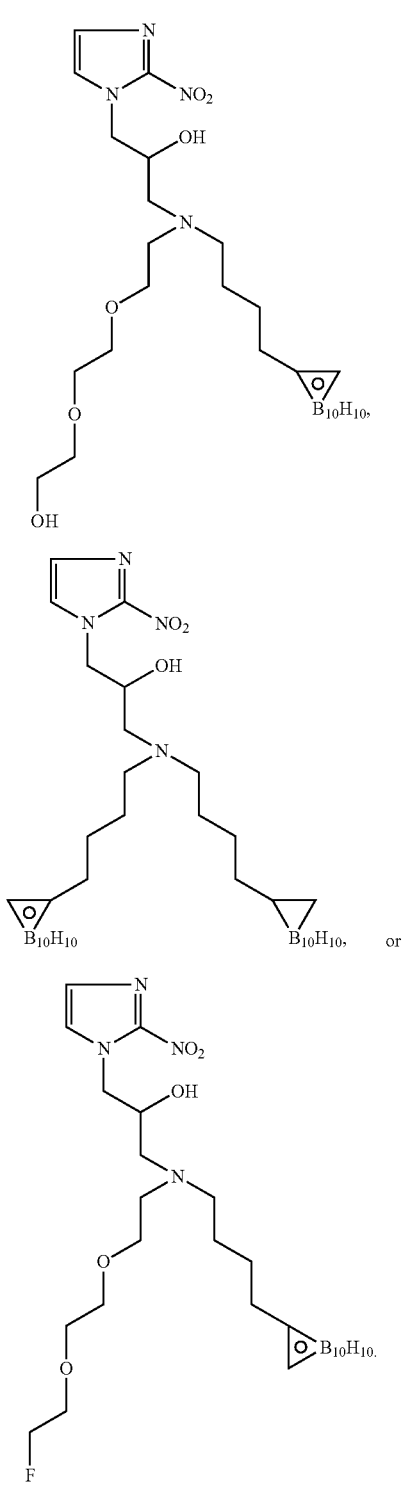

V

VI

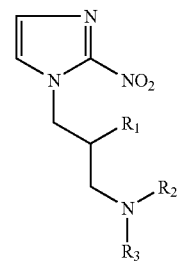

33. The method of claim 29, wherein said halogen is $^{19}F$.

34. The method of claim 29, wherein said compound is administered with a pharmaceutically acceptable carrier or excipient.

35. The method of claim 29, wherein said hypoxic cells are associated with a solid tumor.

36. The method of claim 35, wherein said solid tumor is a glioblastoma, gliosarcoma, or melanoma.

37. A compound having the structure of formula I and pharmaceutically acceptable salts thereof wherein:

R1 is a halogen, positron emitting radionuclide, non-metal, lower alkyl substituted to contain a halogen, lower alkyl substituted to contain a positron emitting radionuclide, lower alkyl substituted to contain a non-metal, tosylate, mesylate, tryflate, hydrogen, or hydroxyl; and R2 and R3 are independently selected from a hydrogen, lower alkyl, allyl, alkenyl, alkynyl, hydroxyalkyl, heteroalkyl, polyether, and polyether with a terminal heteroatom and wherein at least one of R2 or R3 comprises a boron cluster and, optionally, a therapeutic agent, cytotoxic agent, detectable label, or chelating group.

38. The compound of claim 1, wherein said therapeutic agent is a gold particle.

* * * * *

UNITED STATES PATENT AND TRADEMARK OFFICE
CERTIFICATE OF CORRECTION

PATENT NO.         : 7,842,278 B2
APPLICATION NO.    : 11/588634
DATED              : November 30, 2010
INVENTOR(S)        : Lee et al.

It is certified that error appears in the above-identified patent and that said Letters Patent is hereby corrected as shown below:

Column 3, Line 41, replace "dolistatin" with --dolastatin--.

Column 6, Line 45, replace "subsituents" with --substituents--.

Column 9, Line 30, replace "moeity" with --moiety--.

Column 11, Line 39, replace "conjuction" with --conjunction--.

Column 20, Line 25 replace "Technetium $^{99}$mTc Antimony" with --Technetium $^{99m}$Tc Antimony--;

Lines 27-28, replace "Technetium $^{99}$mTc Etidronate; Technetium $^{99}$mTc Exametazime; Technetium $^{99}$mTc Furifosmin" with --Technetium $^{99m}$Tc Etidronate; Technetium $^{99m}$Tc Exametazime; Technetium $^{99m}$Tc Furifosmin--;

Lines 30-33, replace "Technetium $^{99}$mTc Medronate; Technetium $^{99}$mTc Medronate Disodium; Technetium $^{99}$mTc Mertiatide; Technetium $^{99}$mTc Oxidronate; Technetium $^{99}$mTc Pentetate" with --Technetium $^{99m}$Tc Medronate; Technetium $^{99m}$Tc Medronate Disodium; Technetium $^{99m}$Tc Mertiatide; Technetium $^{99m}$Tc Oxidronate; Technetium $^{99m}$Tc Pentetate--;

Lines 34-36, replace "Technetium $^{99}$mTc Siboroxime; Technetium $^{99}$mTc; Succimer; Technetium $^{99}$mTc Sulfur Colloid" with --Technetium $^{99m}$Tc Siboroxime; Technetium $^{99m}$Tc Succimer; Technetium $^{99m}$Tc Sulfur Colloid--;

Signed and Sealed this
Fourteenth Day of February, 2012

David J. Kappos
*Director of the United States Patent and Trademark Office*

CERTIFICATE OF CORRECTION (continued)

Column 20, Line 37, replace "Technetium $^{99}$mTc Tiatide" with --Technetium $^{99m}$Tc Tiatide--.

Column 22, Line 44, replace "51Cr, 67Ga, 68Ga" with --$^{51}$Cr, $^{67}$Ga, $^{68}$Ga--;

Line 45, replace "$^{816}$Re" with --$^{186}$Re--;

Line 61, replace "relaxtivity" with --relaxivity--.

Column 25, Line 16, replace "coca" with --cocoa--.

Column 27, Lines 24-28, replace "In order to increase the solubility of boronated compound, a polyether, 2- [-2] (2-Amino-ethoxy)-ethanol chain was employed as the linker and coupled to the 2-nitroimidazole moiety to give the intermediate (15) which was then couple with the carboranyl linker to give the desired compound 16 (111)." with --The 2-nitroimidazole chloride (5) was converted into primary amine by the Gabriel reaction. The amine (9) was then alkylated with (4) to give the boronated compounds (10, 11, 12% yield from 5) and (11, V, 1.2% yield from 5).--.

Column 28, Line 45, replace "10" with --11--;

Lines 46-50, replace "Step a: NaN3/NaI/DMF, 50°C., 2 h, 90%. Step b: I Ph3P/THF, 50° C., 2 h, ii: H2O, 50° C., 2 h, 60%. Step c: 5/EtOH/Et3N, reflux, 5 h, 30%. Step d: 4/CH3CN, 75° C., 4 h, 40%. Step e: 2-nitro-1-(oxiranylmethyl)-1H-imidazole (CAS#: 13551-90-1)/CH3CN, 85°C., 12 h, 30%." with --Step a: DMF, 85°C, 2h, 87%. Step b: i: 55%NH2-NH2/EtOH, reflux, 2h; ii: 10%KOH, 70%. Step c: 4/CH3CN, reflux, 18h, 20%. Step d: 4/DMF, 85°C, 8h, 10%.--.

Column 29, Line 45, insert --Step a: NaN3/NaI/DMF, 50° C, 2h, 90%. Step b: i: Ph3P/THF, 50°C, 2h, ii: H$_2$O, 50°C, 2h, 60%. Step c: 5/EtOH/Et3N, reflux, 5h, 30%. Step d: 4/CH$_3$CN, 75°C, 4h, 40%. Step e: 2-nitro-1-(oxiranylmethyl)-1H-imidazole (CAS#: 13551-90-1)/CH$_3$CN, 85°C, 12h, 30%.--.

Column 31, Line 22, insert the number --16-- directly below compound 16;

Line 46, insert a new line to separate compounds 16 and 17.

Column 32, Line 24, replace "Prpanol" with --Propanol--.

CERTIFICATE OF CORRECTION (continued)
U.S. Pat. No. 7,842,278 B2

Column 33, Line 65, replace "1,2-3.1" with --1.2-3.1--.

Column 36, Lines 61-62, replace "(m, 4, N" with --(m, 4H, N--.

In Claim 10, Column 38, Lines 44-48, replace "$^{11}$C, $^{13}$N, $^{15}$O, $^{18}$F, $^{52}$Fe, $^{55}$CO, $^{61}$Cu, $^{62}$Cu, $^{64}$Cu, $^{67}$Cu, $^{67}$Ga, $^{68}$Ga, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{111}$In, $^{120}$I, $^{123}$I, $^{124}$I, $^{125}$I, $^{131}$I, $^{122}$Xe, $^{175}$Lu, $^{154}$Gd, $^{71}$As, $^{74}$As, $^{76}$Br, X$^{175}$Lu, $^{154}$Gd, $^{155}$Gd, $^{156}$Gd, $^{157}$Gd, $^{158}$Gd, $^{94m}$Tc, $^{94}$Tc, and $^{99m}$Tc" with --$^{11}$C, $^{13}$N, $^{15}$O, $^{18}$F, $^{52}$Fe, $^{55}$Co, $^{61}$Cu, $^{62}$Cu, $^{64}$Cu, $^{67}$Cu, $^{67}$Ga, $^{68}$Ga, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{111}$In, $^{120}$I, $^{123}$I, $^{124}$I, $^{125}$I, $^{131}$I, $^{122}$Xe, $^{175}$Lu, $^{154}$Gd, $^{155}$Gd, $^{156}$Gd, $^{157}$Gd, $^{158}$Gd, $^{94m}$Tc, $^{94}$Tc, and $^{99m}$Tc--.

In Claim 32, Column 43, Lines 23-39, replace

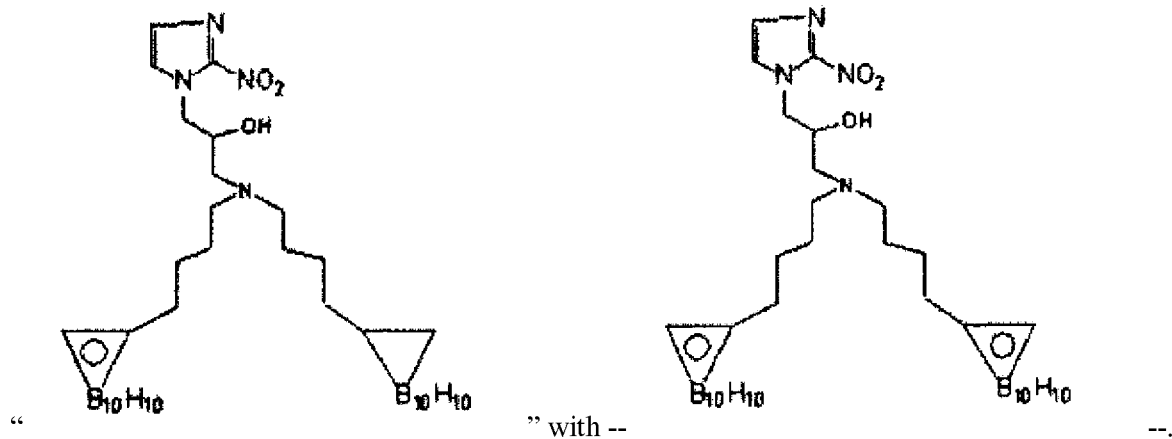

" with -- --.